United States Patent [19]

Janssens et al.

[11] Patent Number: 5,008,268

[45] Date of Patent: Apr. 16, 1991

[54] 2-AMINOPYRIMIDINONE DERIVATIVES

[75] Inventors: Frans E. Janssens, Bonheiden; Ludo E. J. Kennis, Turnhout; Francois M. Sommen, Wortel; Ann C. J. Dierckx, Kasterlee, all of Belgium

[73] Assignee: Janssen Pharmaceutica N.V., Beerse, Belgium

[21] Appl. No.: 456,391

[22] Filed: Dec. 26, 1989

[30] Foreign Application Priority Data

Jan. 9, 1989 [GB] United Kingdom ............... 8900380

[51] Int. Cl.$^5$ .................. A61K 31/505; A61K 31/52; C07D 401/14; C07D 403/14
[52] U.S. Cl. .................................... 514/272; 514/258; 514/261; 514/262; 514/265; 514/266; 514/254; 514/253; 514/2 R; 544/295; 544/296; 544/320; 544/321; 544/262; 544/264; 544/265; 544/276; 544/277; 544/280; 540/599; 540/600; 540/601
[58] Field of Search ............... 544/295, 296, 320, 264, 544/277; 540/599; 514/272, 262, 254

[56] References Cited

U.S. PATENT DOCUMENTS

| 4,219,559 | 8/1980 | Janssens et al. | 424/267 |
|---|---|---|---|
| 4,556,660 | 12/1985 | Janssens et al. | 514/272 |
| 4,588,722 | 5/1986 | Janssens et al. | 514/228 |
| 4,634,704 | 1/1987 | Janssens et al. | 514/253 |
| 4,695,569 | 9/1987 | Janssens et al. | 514/258 |
| 4,695,575 | 9/1987 | Janssens et al. | 514/322 |
| 4,835,161 | 5/1989 | Janssens et al. | 514/303 |

FOREIGN PATENT DOCUMENTS

| 0206415 | 6/1986 | European Pat. Off. . |
|---|---|---|
| 0282133 | 3/1988 | European Pat. Off. . |
| 0297661 | 6/1988 | European Pat. Off. . |
| 0297742 | 6/1988 | European Pat. Off. . |
| 0307014 | 7/1988 | European Pat. Off. . |

Primary Examiner—John M. Ford
Attorney, Agent, or Firm—Charles J. Metz

[57] ABSTRACT

2-Amino-pyrimidininone derivatives possessing antihistaminic and serotonin-antagonistic properties. Compositions containing these compounds as the active ingredient and a method of treating subjects from allergic diseases.

18 Claims, No Drawings

2-AMINOPYRIMIDINONE DERIVATIVES

BACKGROUND OF THE INVENTION

In U.S. Pat. No. 4,219,559 there are described a number of antihistaminic 1-substituted N-heterocyclyl-4-piperidinamines. In U.S. Pat. Nos. 4,556,660; 4,634,704; 4,695,575 and 4,588,722 there are described a further series of N-heterocyclyl-4-piperidinamines as antihistaminics and serotonin antagonists. In EP-A-0,151,826; 0,206,415; 0,282,133; 0,295,742 and 0,297,661 there are disclosed a number of structurally related compounds as antihistaminics and serotonin antagonists.

The compounds of the present invention differ therefrom by the fact that they invariably are substituted with a 2-aminopyrimidinone containing moiety.

DESCRIPTION OF THE INVENTION

The present invention is concerned with novel 2-aminopyrimidinone derivatives having the formula

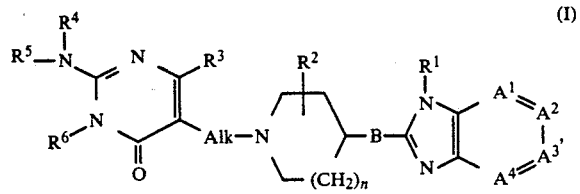

the pharmaceutically acceptable addition salts thereof, and the stereochemically isomeric forms thereof, wherein $-A^1=A^2-A^3=A^4-$ is a bivalent radical having the formula

| | |
|---|---|
| $-CH=CH-CH=CH-$, | (a-1) |
| $-N=CH-CH=CH-$, | (a-2) |
| $-CH=N-CH=CH-$, | (a-3) |
| $-CH=CH-N=CH-$, | (a-4) |
| $-CH=CH-CH=N-$, | (a-5) |
| $-N=CH-N=CH-$ or | (a-6) |
| $-CH=N-CH=N-$, | (a-7) | wherein one or two hydrogen atoms of said radicals (a-1) to (a-7) each independently from one another may be replaced by halo, $C_{1-6}$alkyl, $C_{1-6}$alkyloxy, hydroxy or trifluoromethyl;

$R^1$ is hydrogen, $C_{1-10}$alkyl, $C_{3-6}$cycloalkyl, $Ar^1$, mono- and di($Ar^1$)-$C_{1-6}$alkyl, or a radical of formula $-Alk-G-R^7$; wherein G is O or S; and $R^7$ is hydrogen; $C_{2-6}$alkenyl optionally substituted with $Ar^2$; $C_{3-6}$alkynyl; $C_{1-6}$alkyl optionally substituted with $Ar^1$, hydroxy, $C_{1-6}$alkyloxy, carboxyl or $C_{1-6}$alkyloxycarbonyl;

B is $NR^8$, $CH_2$, O, S, SO or $SO_2$; said $R^8$ being hydrogen, $C_{1-6}$alkyl, $C_{3-6}$cycloalkyl, $C_{1-6}$alkylcarbonyl, $C_{1-6}$alkyloxycarbonyl or $Ar^2$-$C_{1-6}$alkyl;

$R^2$ is hydrogen or $C_{1-6}$alkyl;

n is 0, 1 or 2;

each Alk independently is $C_{1-6}$alkanediyl;

$R^3$ is hydrogen or $C_{1-6}$alkyl;

$R^4$ is hydrogen, $C_{1-6}$alkyl optionally substituted with $Ar^2$, pyridinyl, furanyl, 5-methyl-2-furanyl or $C_{1-6}$alkyloxy;

$R^5$ is hydrogen, $C_{1-6}$alkyl, $C_{1-6}$alkylaminocarbonyl or $Ar^2$-aminocarbonyl;

$R^6$ is hydrogen or $C_{1-6}$alkyl; or $R^5$ and $R^6$ taken together may form a bivalent radical of formula

| | |
|---|---|
| $-CH_2-CH_2-$, | (b-1) |
| $-CH_2-CH_2-CH_2-$, | (b-2) |
| $-CH=CH-$, | (b-3) |
| $-CH=N-$, | (b-4) |
| $-N=CH-$ or | (b-5) |
| $-N=CH-CH_2-$, | (b-6) | wherein one or where possible two hydrogen atoms of said radicals (b-1) to (b-6) each independently from one another may be replaced by $C_{1-6}$alkyl;

$Ar^1$ is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl; thienyl; halothienyl; furanyl optionally substituted with $C_{1-6}$alkyl and/or hydroxy$C_{1-6}$alkyl; pyridinyl; pyrimidinyl; pyrazinyl; thiazolyl; or imidazolyl optionally substituted with $C_{1-6}$alkyl; and $Ar^2$ is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

The compounds of formula (I) wherein $R^1$, $R^4$, $R^5$, $R^6$ and/or $R^8$ are hydrogen may also exist in their tautomeric forms. Such forms although not explicitly indicated in the above formula are intended to be included within the scope of the present invention.

As used in the foregoing definitions "halo" is generic to fluoro, chloro, bromo and iodo; "$C_{1-6}$alkyl" defines straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" defines $C_{1-6}$alkyl radicals as defined hereinabove, and the higher homologs thereof having from 7 to 10 carbon atoms; "$C_{3-6}$cycloalkyl" is generic to cyclopropyl, cyclobutyl, cyclopentyl and cyclohexyl; "$C_{2-6}$alkenyl" defines straight and branch chained hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{3-6}$alkynyl" defines straight and branch chained hydrocarbon radicals containing one triple bond and having from 3 to 6 carbon atoms such as, for example, propargyl, 2-butynyl, 3-butynyl, 2-pentynyl, 3-pentynyl or 4-pentynyl and the like; and when a $C_{3-6}$alkenyl or $C_{3-6}$alkynyl is substituted on a heteroatom, then the carbon atom of said $C_{3-6}$alkenyl or $C_{3-6}$alkynyl connected to said heteroatom preferably is saturated; "$C_{1-6}$alkanediyl" defines bivalent straight or branch chained hydrocarbon radicals containing from 1 to 6 carbon atoms such as, for example, 1,2-ethanediyl, 1,3-propanediyl, 1,4-butanediyl, 1,5-pentanediyl, 1,6-hexanediyl and the branched isomers thereof.

Said addition salts as mentioned hereinabove are meant to comprise the therapeutically active non-toxic addition salt forms which the compounds of formula (I) are able to form. The latter can conveniently be obtained by treating the base form with such appropriate acids as inorganic acids, for example, hydrohalic acids, e.g. hydrochloric, hydrobromic and the like, sulfuric acid, nitric acid, phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted into their therapeutically active non-toxic metal or amine addition salt forms by treatment with appropriate organic or inorganic bases.

The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure. Each of these chiral centers may be indicated by the stereochemical descriptors R and S, this R and S notation corresponding to the rules described in Pure Appl. Chem. 1976, 45, 11–30.

Diastereoisomers may be separated by physical separation methods such as selective crystallization and chromatographic techniques, e.g., counter current distribution, liquid chromatography and the like; and enantiomers may be separated from each other following art-known resolution methods, for example, by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereoselective methods of preparation. These methods will advantageously employ enantiomerically pure starting materials.

Stereochemically isomeric forms of the compounds of formula (I) are naturally intended to be embraced within the scope of the invention.

A particular group of compounds are those compounds of formula (I) wherein
—$A^1$=$A^2$—$A^3$=$A^4$— is a bivalent radical (a-1) or (a-2);
$R^1$ is $Ar^1$-$C_{1-6}$alkyl or a radical of formula —Alk—G—$R^7$; wherein
G is O; and
$R^7$ is $C_{1-6}$alkyl;
B is NH or $CH_2$;
$R^2$ is hydrogen;
n is 1 or 2; and
$R^3$ is $C_{1-6}$alkyl.

Another particular subgroup of compounds comprises those compounds of formula (I) wherein
$R^1$ is hydrogen, ($Ar^1$)$C_{1-6}$alkyl or $C_{1-6}$alkyloxy$C_{1-6}$alkyl; and/or
B is NH, $CH_2$, O or S; and/or
$R^2$ is hydrogen; and/or
$R^3$ is $C_{1-6}$alkyl; and/or
$R^5$ is hydrogen, $C_{1-6}$alkylaminocarbonyl or phenylaminocarbonyl; and/or
$R^6$ is $C_{1-6}$alkyl; or
$R^5$ and $R^6$ taken together may form a bivalent radical of formula (b-1) to (b-6) wherein one hydrogen atom of said radicals (b-1) to (b-6) may be replaced by $C_{1-6}$alkyl; and/or
$Ar^1$ is phenyl optionally substituted with halo; furanyl optionally substituted with $C_{1-6}$alkyl and/or hydroxy$C_{1-6}$alkyl; pyridinyl; or thiazolyl.

Interesting compounds among the compounds of formula (I) and/or in the particular subgroups defined hereinabove, are those wherein
—$A^1$=$A^2$—$A^3$=$A^4$— is a bivalent radical having the formula (a-1) wherein one or two hydrogen atoms each independently from one another may be replaced by halo, $C_{1-4}$alkyl or $C_{1-4}$alkyloxy; (a-2); (a-6) wherein one hydrogen atom may be replaced by $C_{1-4}$alkyl; or (a-7) wherein one hydrogen atom may be replaced by hydroxy; and/or
$R^1$ is hydrogen, ($Ar^1$)$C_{1-4}$alkyl or $C_{1-4}$alkyloxy$C_{2-4}$alkyl; and/or
Alk is 1,2-ethanediyl; and/or
$R^3$ is $C_{1-4}$alkyl; and/or
$R^4$ is hydrogen, $C_{1-6}$alkyl, phenyl$C_{1-4}$alkyl, pyridinyl$C_{1-4}$alkyl, 5-methyl-2-furanyl$C_{1-4}$alkyl or $C_{1-4}$alkyloxy$C_{2-4}$alkyl; and/or
$R^5$ is hydrogen, $C_{1-4}$alkylaminocarbonyl or phenylaminocarbonyl; and/or
$R^6$ is $C_{1-6}$alkyl; or
$R^5$ and $R^6$ taken together may form a bivalent radical of formula (b-1); (b-3); (b-5) or (b-6), wherein one hydrogen atom of said radicals (b-3), (b-5) and (b-6) may be replaced by $C_{1-4}$alkyl; and/or
$Ar^1$ is phenyl optionally substituted with halo; furanyl substituted with $C_{1-4}$alkyl and/or hydroxy$C_{1-4}$alkyl; pyridinyl; or thiazolyl.

Particularly interesting compounds are those interesting compounds wherein
—$A^1$=$A^2$—$A^3$=$A^4$— is a bivalent radical having the formula (a-1) or (a-2); and/or
$R^1$ is 4-fluorophenylmethyl; 5-methyl-2-furanylmethyl; 5-hydroxymethyl-2-furanylmethyl or 2-ethoxyethyl;
B is NH or $CH_2$; and/or
n is 1; and/or
$R^3$ is methyl; and/or
$R^4$ is hydrogen, $C_{1-6}$alkyl; phenylmethyl; pyridinylmethyl; 5-methyl-2-furanylmethyl or 2-ethoxyethyl; and/or
$R^5$ is hydrogen, methylaminocarbonyl or phenylaminocarbonyl; and/or
$R^6$ is $C_{1-6}$alkyl; or
$R^5$ and $R^6$ taken together may form a bivalent radical of formula (b-3) or (b-6) wherein one hydrogen atom of said bivalent radicals may be replaced by methyl.

More particularly interesting compounds are those particularly interesting compounds wherein
$R^4$ is hydrogen, $C_{1-4}$alkyl, phenylmethyl, 2-pyridinylmethyl or 2-ethoxyethyl; and/or
$R^5$ is hydrogen; and/or
$R^6$ is methyl; or
$R^5$ and $R^6$ taken together may form a bivalent radical of formula (b-3) wherein one hydrogen atom of said bivalent radical may be replaced by methyl.

The most interesting compounds of formula (I) are 2-amino-5-[2-[4-[[1-[[5-hydroxymethyl-2-furanyl]methyl]-1H-benzimidazol-2-yl]amino]-1-piperidinyl]ethyl]-3,6-dimethyl-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2(methylamino)-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-[(2-pyridinylmethyl)amino]-4(3H-pyrimidinone,
5-[2-[4-[[1-[[5-(hydroxymethyl)-2-furanyl]methyl]-1H-
benzimidazol-2-yl]amino]-1-piperidinyl]ethyl]-3,6-
dimethyl-2-(propylamino)-4(3H)-pyrimidinone and the
pharmaceutically acceptable acid addition salts and the
possible stereochemically isomeric forms thereof.

In order to simplify the structural representations of
some of the compounds and intermediates in the following preparations the 2-aminopyrimidinone moiety
wherein $R^3$, $R^4$, $R^5$, $R^6$ and Alk are as defined under
formula (I) will hereinafter be represented by the symbol L; in a similar manner the moiety containing the
imidazole group fused to a benzene, pyridine or pyrimidine ring and wherein $R^1$ is as defined hereinabove will
hereinafter be represented by the symbol Q.

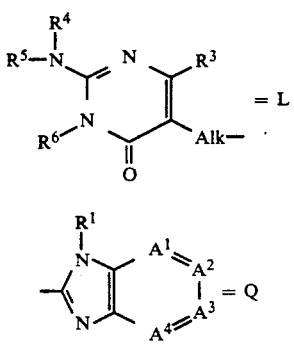

The compounds of formula (I) can generally be prepared by N-alkylating an intermediate of formula (II)
with an alkylating reagent of formula (III), wherein $W^1$
is a reactive leaving group such as, for example, halo,
e.g. chloro, bromo and the like; or a sulfonyloxy group,
e.g. methanesulfonyloxy, 4-methylbenzenesulfonyloxy
and the like leaving groups.

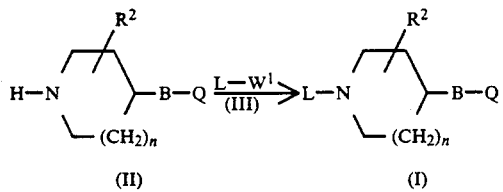

Said N-alkylation can conveniently be carried out by
mixing the reactants, optionally in a reaction-inert solvent such as, for example, water; an aromatic solvent,
e.g. benzene, methylbenzene, dimethylbenzene, chlorobenzene, methoxybenzene and the like; a $C_{1-6}$alkanol,
e.g. methanol, ethanol, 1-butanol and the like; a ketone,
e.g. 2-propanone, 4-methyl-2-pentanone and the like; an
ester, e.g. ethyl acetate, γ-butyrolactone and the like; an
either, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone,
1,1,3,3-tetramethylurea, 1-methyl-2-pyrrolidinone, nitrobenzene, acetonitrile and the like; or a mixture of
such solvents. The addition of an appropriate base such
as, for example, an alkali metal or an earth alkaline
metal carbonate, hydrogen carbonate, hydroxide, oxide,
carboxylate, alkoxide, hydride or amide, e.g. sodium
carbonate, sodium hydrogen carbonate, potassium carbonate, sodium hydroxide, calcium oxide, sodium acetate, sodium methoxide, sodium hydride, sodium amide
and the like, or an organic base such as, for example, a
tertiary amine, e.g. N,N-diethylethanamine, N-(1-methylethyl)-2-propanamine, 4-ethylmorpholine, 1,4-diazabicyclo[2.2.2]octane, pyridine and the like, may
optionally be used to pick up the acid which is formed
during the course of the reaction. Further, it may be
advantageous to convert the intermediate of formula
(II) first into a suitable salt form thereof such as, for
example, an alkali or earth alkaline metal salt, by reacting (II) with an appropriate base as defined hereinabove
and subsequently using said salt form in the reaction
with the alkylating reagent of formula (III). In some
instances the addition of an iodide salt, preferably an
alkali metal iodide, or a crown ether, e.g. 1,4,7,10,13,16-hexaoxacyclooctadecane and the like, may be appropriate. Stirring and somewhat elevated temperatures may
enhance the rate of the reaction; more in particular the
reaction may be conducted at the reflux temperature of
the reaction mixture. Additionally, it may be advantageous to conduct said N-alkylation under an inert atmosphere such as, for example, oxygen-free argon or nitrogen gas. Alternatively, said N-alkylation may be carried
out by applying art-known conditions of phase transfer
catalysis reactions. Said conditions comprise stirring the
reactants, with an appropriate base and optionally
under an inert atmosphere as defined hereinabove, in
the presence of a suitable phase transfer catalyst such as,
for example, a trialkylphenylmethylammonium, tetraalkylammonium, tetraalkylphosphonium, tetraarylphosphonium halide, hydroxide, hydrogen sulfate and
the like catalysts. Somewhat elevated temperatures may
be appropriate to enhance the rate of the reaction.

The compounds of formula (I) wherein $R^1$ is other
than hydrogen, said $R^1$ being represented by $R^{1-a}$ and
said compounds by formula (I-a) can also be prepared
by N-alkylating a compound of formula (I) wherein $R^1$
is hydrogen, said compound being represented by formula (I-b), with an appropriate reagent of formula $R^{1-a}—W^1$, wherein $W^1$ is a reactive leaving group as defined hereinabove.

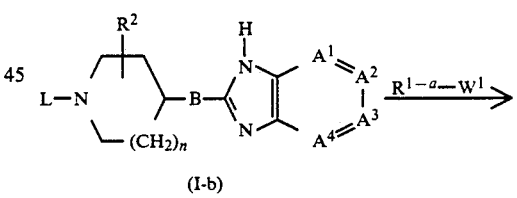

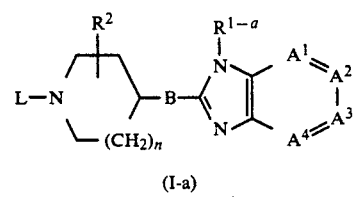

Said N-alkylation reaction is conveniently conducted in
a reaction-inert solvent such as, for example, an aromatic hydrocarbon, e.g., benzene, methylbenzene, dimethylbenzene, and the like; an alkanol, e.g., methanol,
ethanol, 1-butanol and the like; a ketone, e.g., 2-propanone, 4-methyl-2-pentanone and the like; an ether, e.g.,
tetrahydrofuran, 1,4-dioxane, 1,1'-oxybisethane and the
like; a dipolar aprotic solvent, e.g., N, N-dimethylformamide, N,N-dimethylacetamide, dimethylsulfoxide,
nitrobenzene, 1-methyl-2-pyrrolidinone, and the like.

The addition of an appropriate base such as, for example, an alkali or an earth alkaline metal carbonate, hydrogen carbonate, hydroxide or oxide, e.g., sodium carbonate, sodium hydrogen carbonate, potassium carbonate, sodium hydroxide, calcium carbonate, calcium hydroxide, calcium oxide and the like; or an organic base, such as, for example, a tertiary amine, e.g., N,N-diethylethanamine, N-(1-methylethyl)-2-propanamine, 4-ethyl-morpholine and the like may be utilized to pick up the acid which is liberated during the course of the reaction. In some instances the addition of a iodide salt, preferably an alkali metal iodide, is appropriate. Somewhat elevated temperatures and stirring may enhance the rate of the reaction.

The compounds of formula (I) wherein $R^1$ is hydroxymethylfuranylalkyl, said compounds being represented by formula (I-a-1), can also be prepared by reducing a alkyloxycarbonylfuranylalkyl derivative of formula (IV).

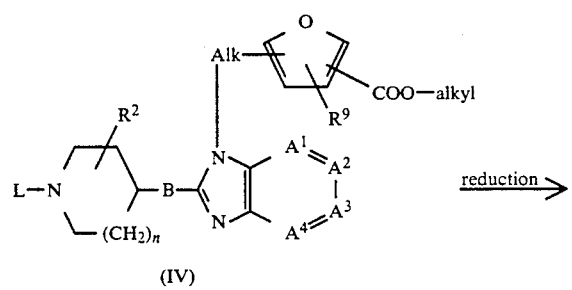

(IV)

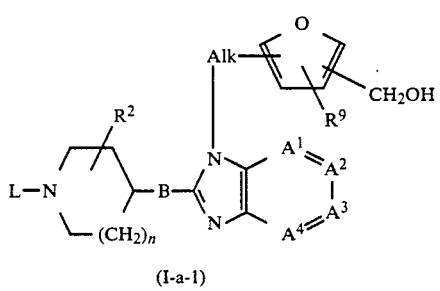

(I-a-1)

In formulae (IV) and (I-a-1), $R^9$ represents hydrogen or $C_{1-6}$alkyl. Said reduction reaction can conveniently be conducted by reacting (IV) with a reducing agent such as, for example, lithium aluminum hydride, lithium borohydride, di(1-methylpropyl) aluminum hydride, aluminum hydride, sodium bis(2-methoxyethoxy) aluminum hydride, lithium trialkoxyalanes and the like reducing agents, in a reaction-inert solvent such as, for example, an ether, e.g. 1,1'-oxybisethane, tetrahydrofuran, 1,4-dioxane, 2,2'-oxybispropane, 1,2-dimethoxyethane, 1,1'-oxybis(2-methoxyethane) and the like solvents. In order to enhance the rate of said reduction, the reaction mixture may advantageously be heated, in particular at the reflux temperature.

The compounds of formula (I) may also be prepared by reacting an intermediate of formula (V) with an appropriately substituted diamine of formula (VI) in a reaction-inert solvent.

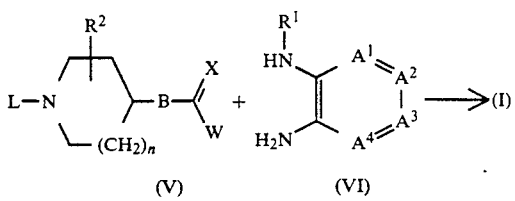

In this and the following reaction schemes W represent an appropriate reactive leaving group such as, for example, halo, e.g. chloro, bromo or iodo; $C_{1-6}$alkyloxy; $C_{1-6}$alkylthio, $Ar^2$—O— or $Ar^2$—S—; and X denotes O, S or NH.

The derivatives of formula (V) wherein B is $CH_2$, W is halo and X is O may be generated in situ, for example, by halogenating the corresponding carboxylic acid with thionyl chloride, phosphorous trichloride, phosphoryl chloride, polyphosphoric acid and the like reagents. The reaction of (V) with (VI) may be conducted in a suitable reaction-inert solvent such as, for example, a hydrocarbon, e.g., benzene, hexane and the like; an ether, e.g., 1,1'-oxybisethane, tetrahydrofuran and the like; a ketone, e.g., 2-propanone, 2-butanone and the like; and alcohol, e.g., methanol, ethanol, 2-propanol, 1-butanol and the like; a halogenated hydrocarbon, e.g., trichloromethane, dichloromethane and the like; an organic acid, e.g., acetic acid, propanoic acid and the like; a dipolar aprotic solvent e.g., N,N-dimethylformamide, N,N-dimethylacetamide and the like; or a mixture of such solvents. Depending upon the nature of the solvent and W it may be appropriate to add to the reaction mixture a base such as is commonly employed in the art of conducting N-alkylation reactions and/or a iodide salt such as an alkali metal iodide. Elevated temperatures and stirring may enhance the reaction rate. In some instances the reaction of (V) with (VI) may first yield an intermediate of formula (V-a) which subsequently may be cyclized to the desired compound of formula (I), either in situ or, if desired, after isolation and purification.

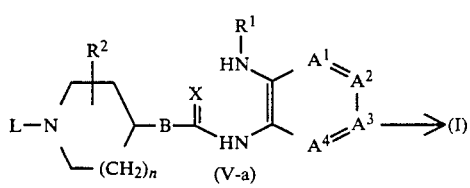

The compounds of formula (I) can also be prepared by reacting an intermediate of formula (VII) with an intermediate of formula (VIII) following art-known substitution reaction procedures. In (VII) and hereinafter M is, depending upon the nature of B, hydrogen or an appropriate alkali metal or earth alkaline metal; for example, the group —B—M may represent —OH, —ONa, —SH, —SNa, —$NHR^8$, —$CH_2$—Li, —$CH_2$—Mg—halide and the like groups.

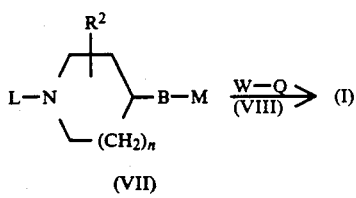

(VII)

In addition, the compounds of formula (I) can also be prepared by reacting an intermediate of formula (IX) with an intermediate of formula (X) wherein M has the previously described meaning. In formula (IX) and hereinafter $W^1$ is an appropriate leaving group as defined hereinabove.

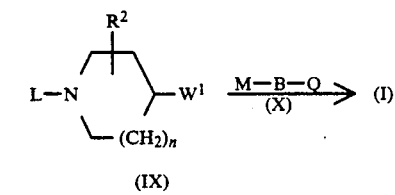

(IX)

The compounds of formula (I) wherein B is —$CH_2$—, said compounds being represented by formula (I-c) can also be prepared by reacting an intermediate of formula (XI) with an intermediate of formula (XII) or alternatively, by reacting an intermediate of formula (XIII) with an intermediate of formula (XIV). In formula (XII) and (XIII) $M^1$ represents an appropriate alkali metal or earth alkaline metal such as, for example, lithium, magnesiumhalide and the like and $W^1$ has the previously defined meaning.

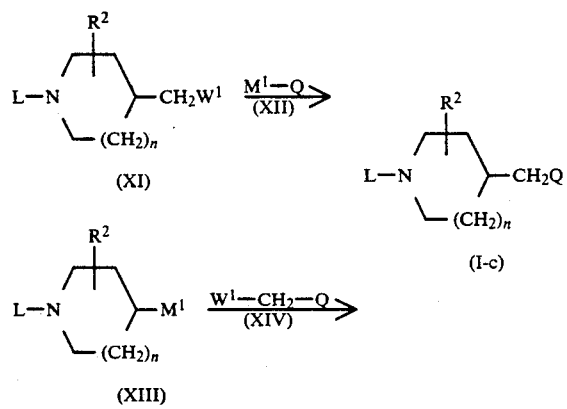

The reactions of (VII), (IX), (XI) and (XIII) with respectively (VIII), (X), (XII) and (XIV) may conveniently be conducted in an appropriate reaction-inert solvent such as for example, an aromatic hydrocarbon, e.g., benzene, methylbenzene and the like; an ether, e.g. 1,4-dioxane, 1,1'-oxybisethane, tetrahydrofuran and the like; a halogenated hydrocarbon, e.g. trichloromethane and the like; N,N-dimethylformamide; N,N-dimethylacetamide; nitrobenzene; dimethylsulfoxide; 1-methyl-2-pyrrolidinone and the like; and when M is hydrogen, said solvent may also be a $C_{1-6}$alkanol, e.g., methanol, ethanol, 1-butanol and the like; a ketone, e.g., 2-propanone, 4-methyl-2-pentanone and the like. In some instances, particularly when B is a heteroatom, the addition of an appropriate base such as, for example, an alkali metal carbonate or hydrogen carbonate, e.g. sodium carbonate, sodium hydrogen carbonate and the like; sodium hydride; or an organic base such as, for example, N,N-diethylethanamine or N-(1-methylethyl)-2-propanamine and/or the addition of a iodide salt, preferably an alkali metal iodide, may be appropriate. Somewhat elevated temperatures and stirring may enhance the rate of the reaction.

The compounds of formula (I) wherein B is —$NR^8$—, said compounds being represented by formula (I-d) can also be prepared by reacting an intermediate of formula (XV) with an intermediate of formula (X) wherein B-M represents a radical —$NHR^8$, said intermediate being represented by formula (X-a), following art-known reductive N-alkylation procedures.

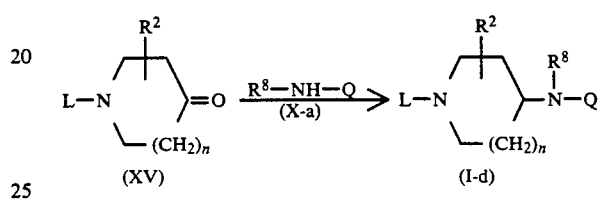

The reaction of (XV) with (X-a) can conveniently be carried out by mixing the reactants in a suitable reaction-inert organic solvent with an appropriate reductant. Preferably, the ketone of formula (XV) is first reacted with the intermediate of formula (X-a) to form an enamine, which optionally may be isolated and further purified, and subsequently reducing said enamine. Suitable solvents are, for example, water; aromatic hydrocarbons, e.g. benzene, methylbenzene, dimethylbenzene and the like; $C_{1-6}$alkanols, e.g. methanol, ethanol, 2-propanol and the like; ethers, e.g. 1,4-dioxane and the like; halogenated hydrocarbons, e.g. trichloromethane and the like; N,N-dimethylformamide; N,N-dimethylacetamide; dimethylsulfoxide and the like; or a mixture of such solvents. Said enamine formation may conveniently be conducted in the presence of an acid such as, for example, 4-methylbenzenesulfonic acid, methanesulfonic acid and the like. Appropriate reductants are for example, metal or complex metal hydrides, e.g. sodium borohydride, sodium cyanoborohydride, lithium aluminum hydride and the like. Alternatively, hydrogen in the presence of a suitable catalyst such as, for example, palladium-on-charcoal, platinum-on-charcoal and the like may be used as reductant. In order to prevent the undesired further hydrogenation of certain functional groups in the reactants and the reaction products it may be advantageous to add an appropriate catalyst poison to the reaction mixture such as, for example, thiophene and the like.

The compounds of formula (I-d) wherein B is —NH—, said compounds being represented by formula (I-d-1) can also be prepared by a cyclodesulfurization reaction of an appropriate thiourea of formula (V-a) wherein X is S, said thiourea being represented by formula (V-a-1), which may be formed in situ by condensing an isothiocyanate of formula (XVI) with a diamine of formula (VI).

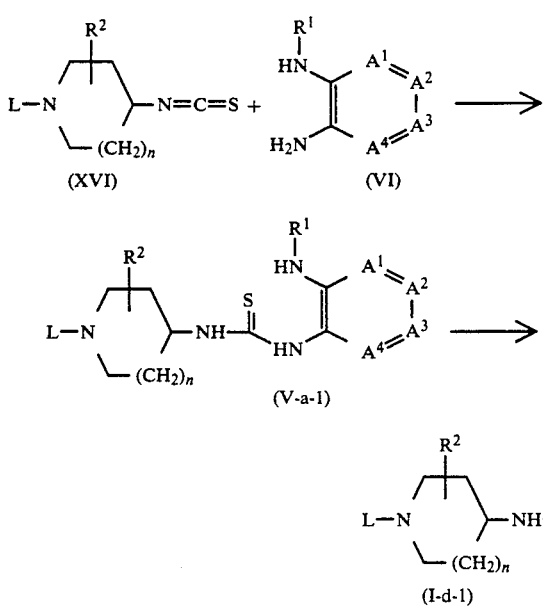

Said cyclodesulfurization reaction may be carried out by reacting (V-a-1) with an appropriate alkyl halide, preferably iodomethane in a suitable reaction-inert organic solvent, e.g., a $C_{1-6}$alkanol such as, methanol, ethanol, 2-propanol and the like. Alternatively, said cyclodesulfurization reaction may also be carried out by the reaction of (V-a-1) with an appropriate metal oxide or salt in an appropriate solvent following art-known procedures. For example, the compounds of formula (I-d-1) can easily be prepared by the reaction of (V-a-1) with a Hg(II) or Pb(II) oxide or salt such as, for example, HgO, $HgCl_2$, $Hg(OAc)_2$, PbO or $Pb(OAc)_2$. In certain instances it may be appropriate to supplement the reaction mixture with a small amount of sulfur. Also methanediimides, especially dicyclohexylcarbodiimide may be used as cyclodesulfurizing agents.

The compounds of formula (I) can also be converted into each other following art-known procedures of functional group transformation. Some examples of such procedures will be cited hereinafter. The compounds of formula (I) wherein B is S may be converted into the corresponding compounds of formula (I) wherein B is SO or $SO_2$ by an appropriate oxidation reaction, e.g., with an oxidating agent such as, for example, potassium periodate, a peroxide, e.g., 3-chlorobenzenecarboperoxoic acid, hydrogen peroxide and the like, in a solvent such as, for example, an ether, e.g., tetrahydrofuran, 1,1'-oxybisethane; a hydrocarbon, e.g., benzene; a halogenated hydrocarbon, e.g., dichloromethane, trichloromethane and the like. Amino groups may be alkylated or acylated following art-known procedures such as, for example, N-alkylation, N-acylation, reductive N-alkylation and the like methods. For example $C_{1-6}$alkyl carbonyl, ($C_{1-6}$alkyl and $Ar^2$) aminocarbonyl and the like groups may be introduced by reacting the starting amine with an appropriate carboxylic acid or a functional derivative thereof such as, for example, an acid halide, a mixed or symmetric acid anhydride and the like; or by reaction with an appropriate ($C_{1-6}$alkyl or $Ar^2$)isocyanate in a reaction-inert solvent such as, for example, an aromatic hydrocarbon, e.g. benzene, methylbenzene, and the like, an halogenated hydrocarbon, e.g. dichloromethane, trichloromethane and the like, an ether, e.g. 1,1'-oxybisethane, tetrahydrofuran, 1,4-dioxane and the like. The compounds of formula (I) containing an amino group substituted with a radical $Ar^2$-$CH_2$, may be hydrogenolyzed by treating the starting compounds with hydrogen in the presence of a suitable catalyst, e.g., palladium-on-charcoal, platinum-on-charcoal, preferably in an alcoholic medium. In all of the foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds and others are new. A number of such preparation methods will be described hereinafter in more detail.

Starting materials such as the intermediates of formulae (II), (VI), (VIII), (X), (XII) and (XIV) can conveniently be prepared following procedures similar to those described in, for example, U.S. Pat. Nos. 4,219,559; 4,335,127; 4,342,870; 4,443,451; 4,634,704; 4,695,575 and 4,588,722, which are incorporated herein by reference.

The intermediates of formulae (V), (VII), (IX), (XI), (XIII), (XV) and (XVI) containing the amino pyrimidinone moiety are novel and can be prepared by N-alkylating an appropriate intermediate of formula (XVII) with a reagent of formula (III).

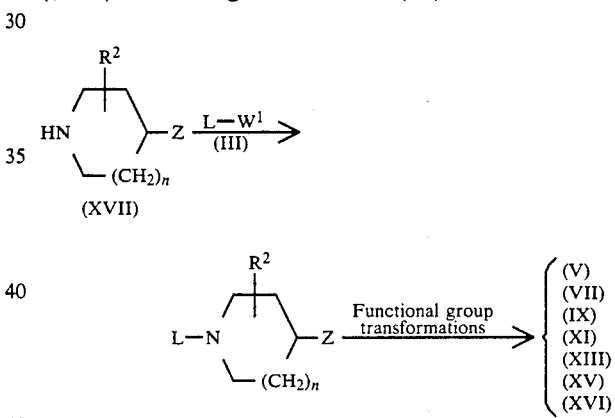

In the above reaction scheme Z generally represents a functional group which may be converted into the desired functionality of the enumerated intermediates following art-known functional group transformation procedures such as deprotection, activation, metalation, oxidation, reduction, hydrolysis, nucleophilic substitution, acylation and the like methods. Alternatively, said functional group transformation reactions may also be conducted on the intermediates (XVI) or the protected derivatives thereof, and subsequently alkylating the thus obtained intermediates with a reagent of formula (III).

The intermediates of formula (III) can generally be prepared from an appropriate alcohol of formula (XVIII) upon treatment with a halogenating reagent such as, for example, a hydrohalic acid, e.g. hydrochloric or hydrobromic acid; thionyl chloride; phosphorous trichloride; phosphoryl chloride; methanesulfonylchloride, triphenylphosphine-tetrahalomethane and the like reagents; or with a sulfonylhalide reagent such as, for example, methanesulfonylchloride, 4-methylbenzenesulfonylchloride and the like.

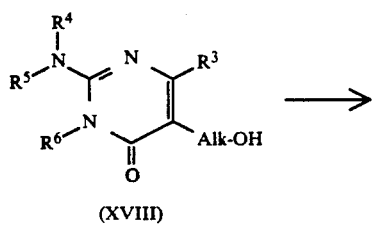

(XVIII)

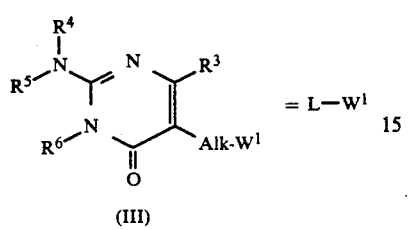

(III)

The intermediates of formula (XVIII) wherein $R^5$ and $R^6$ together form a bivalent radical of formula (b-1) to (b-3) can generally be prepared by condensing an intermediate of formula (XVIII-a) wherein $R^5$ and $R^6$ are hydrogen with an appropriate alkylating reagent. For example, the N-alkylation reaction of intermediate (XVIII-a) with a 1,2-dihaloethane or a 1,3-dihalopropane can yield those intermediates wherein $R^5$ and $R^6$ together form an ethanediyl (XVIII-b-1) or propanediyl (XVIII-b-2) radical.

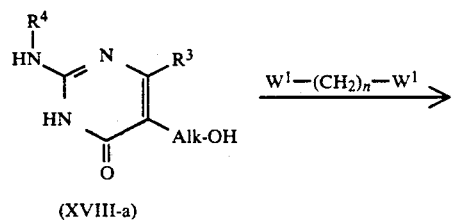

(XVIII-a)

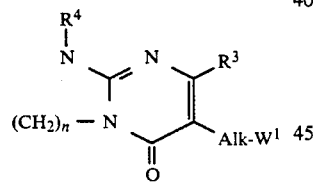

(XVIII-b-1; n = 2)
(XVIII-b-2; n = 3)

Intermediates of formula (XVIII-b-3) can be obtained by condensing (XVIII-a) wherein $R^5$ and $R^6$ are hydrogen, with an α-haloketone or -aldehyde wherein R represents hydrogen or $C_{1-6}$alkyl, in the presence of an appropriate acid or base.

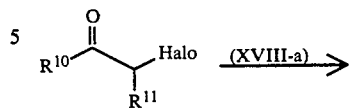

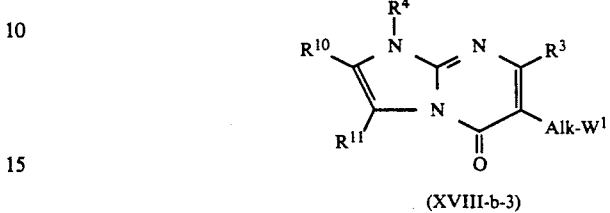

(XVIII-b-3)

The intermediates of formula (XVIII-b-3) and (XVIII-b-4) can also be prepared by condensing an appropriately substituted 2-aminoimidazole ($X^1 = CR^{11}$) or 2-aminotriazole ($X^1 = N$) of formula (XIX) wherein $R^{10}$ and $R^{11}$ each independently represent hydrogen or $C_{1-6}$alkyl, with an α-acyl-lactone (XX) in the presence of an activating reagent such as a halogenating reagent in a reaction-inert solvent. In some instances the hydroxy group may be converted in situ into a halo group, thus directly yielding an alkylating reagent of formula (III) when $W^1$ is halo.

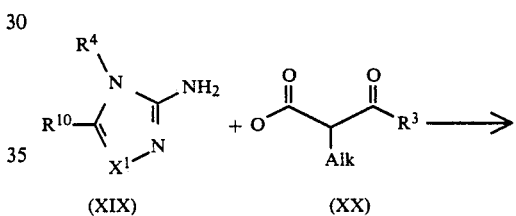

(XIX)        (XX)

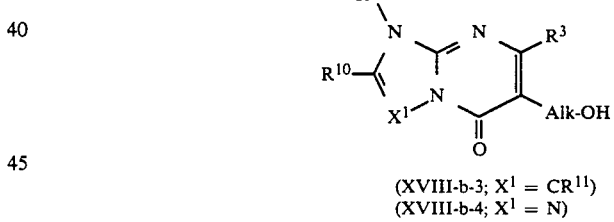

(XVIII-b-3; $X^1 = CR^{11}$)
(XVIII-b-4; $X^1 = N$)

The intermediates of formula (XVIII-b-5) and (XVIII-b-6) can be obtained by condensing the hydrazine derivative (XXI) with respectively an α-haloketone and an orthoester.

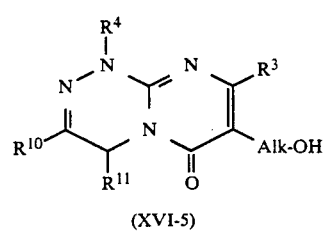

(XVI-5)

-continued

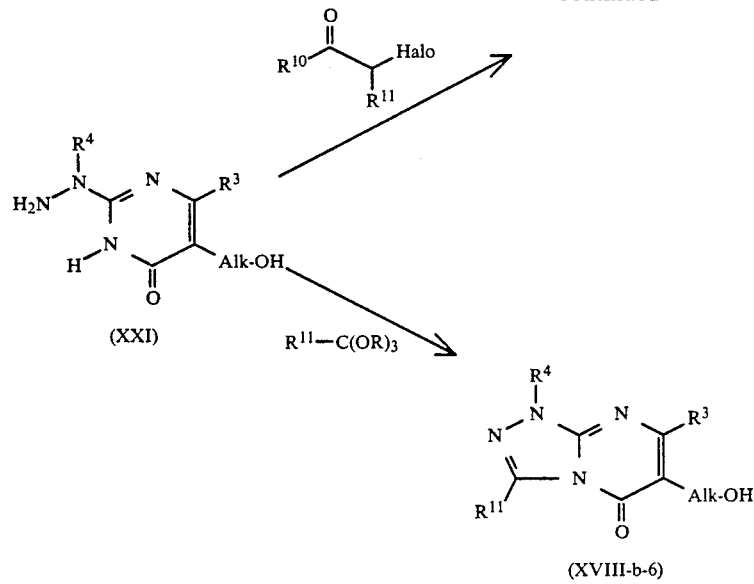

(XXI)

(XVIII-b-6)

The monocyclic aminopyrimidinones of formula (XVIII) and the hydrazine derivative (XXI) can be prepared from an appropriate mercaptopyrimidinone (XXII) by S-alkylating it first to an alkylthio intermediate and subsequently substituting this alkylthio substituent with respectively an amine $R^4R^5NH$ or a hydrazine $R^4NHNH_2$.

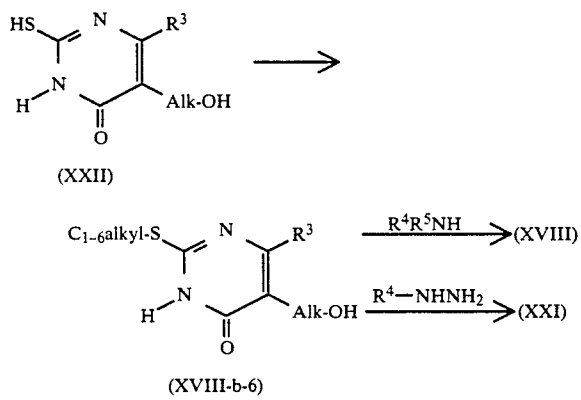

(XXII)

(XVIII-b-6)

The compounds of formula (I), the pharmaceutically acceptable acid addition salts and stereochemically isomeric forms thereof possess useful pharmacological properties. More particularly, they are active antihistaminics which can clearly be demonstrated by, e.g., the results obtained in the "Protection of Rats from Compound 48/80-induced lethality"-test, the "Histamine antagonism in Guinea Pig"-test and the "Ascaris Allergy test in Dogs"-test described in Arch. Int. Pharmacodyn. Ther. 251, 39–51 (1981). Apart from their antihistaminic properties the subject compounds also show peripheral serotonin-antagonism, as can be demonstrated in the "Gastric Lesions induced by compound 48/80 in rats" test and in the combined "Apomorphine, tryptamine, norepinephrine test in rats".

The compounds of formula (I), the pharmaceutically acceptable acid addition salts and stereochemically isomeric forms thereof are particularly attractive due to their enhanced peripheral serotoninergic properties. In view of their antihistaminic and peripheral serotoninergic properties, the compounds of formula (I) and their acid addition salts are very useful in the treatment of allergic diseases such as, for example, allergic rhinitis, allergic conjunctivitis, chronic urticaria, allergic asthma and the like.

In view of their useful pharmacological properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in treating allergic diseases in warm-blooded animals could easily determine the effective amount from the test results presented hereinafter. In general it is contemplated that an effective amount would be from about 0.001 mg/kg to about 100 mg/kg body weight, and more preferably from about 0.01 mg/kg to about 1 mg/kg body weight.

The following examples are intended to illustrate and not to limit the scope of the present invention in all its aspects. Unless otherwise stated all parts therein are by weight.

EXPERIMENTAL PART

A. Preparation of Intermediates

EXAMPLE 1

(a) To a stirred suspension of 90 parts of 5-(2-hydroxyethyl)-2-mercapto-6-methyl-4(3H)-pyrimidinone in 320 parts of methanol were added 90 parts of a sodium methoxide solution 30%. After stirring for 20 minutes, 72 parts of iodomethane were added and the whole was stirred and refluxed for 3 hours. The reaction mixture was evaporated in vacuo and water was added to the residue. The precipitated product was filtered off and crystallized from ethanol, yielding 78 parts (78%) of 5-(2-hydroxyethyl)-6-methyl-2-(methylthio)-4(3H)-pyrimidinone (interm. 1).

(b) A mixture of 160 parts of interm. 1 and ±700 parts of methanamine monoacetate was refluxed for 2 hours. After cooling to 50° C., nitrogen was bubbled through the solution for 1 hour. The reaction mixture was cooled to 10° C. and the whole was poured into 2000 parts of ice water and 100 parts of ammonium hydroxide were added. After 30 minutes, a solid product was filtered off, washed twice with 200 parts of water and twice with 80 parts of acetonitrile and dried, yielding 108.5 parts (74.0%) of 5-(2-hydroxyethyl)-6-methyl-2-(methylamino)-4(3H)-pyrimidinone (interm. 2).

(c) To a stirred mixture of 50.7 parts of interm. 2, 31.8 parts of sodium carbonate and 376 parts of N/-dimethylformamide were added at once 27.75 parts of 1-chloro-2-propanone. The reaction mixture was stirred first for 2 hours at 100° C. and then overnight at room temperature. The precipitate was filtered off and the filtrate was evaporated. The residue was treated with 160 parts of acetonitrile. After cooling to 0° C., the product was filtered off and dried, yielding 32 parts (48.5%) of 5-(2-hydroxyethyl)-6-methyl-2-(methylamino)-3-(2-oxopropyl)-4(3H)-pyrimidinone (interm. 3).

(d) A solution of 38.3 parts of interm. 3 and 250 parts of acetic acid, saturated with hydrogen bromide was stirred overnight at reflux temperature. The solvent was evaporated and the residue was combined with 375 parts of a hydrobromic acid solution 48% in water. The whole was stirred for 5 hours at reflux temperature. After evaporation, the residue was combined with 400 parts of water and treated with 100 parts of an ammonium hydroxide solution. The precipitated product was filtered off, washed with 40 parts of cooled ethanol and dried, yielding 34 parts (74.8%) of 6-(2-bromoethyl)-1,2,7-trimethyl-1H,5H-imidazo[1,2-a]pyrimidin-5-one; mp. 125° C. (interm. 4).

EXAMPLE 2

(a) To a stirred mixture of 64 parts of interm. 2, 80.6 parts of sodium carbonate and 329 parts of N/-dimethylformamide were added 54.5 parts of 1-bromo-2-chloroethane. The reaction mixture was heated for 20 hours at 100° C. After cooling, the precipitate was filtered off and the filtrate was evaporated. The residue was extracted with 450 parts of trichloromethane. The extract was washed twice with 50 parts of water, dried, filtered and evaporated, yielding 15.2 parts (20.8%) of 2,3-dihydro-6-(2-hydroxyethyl)-1,7-dimethyl-1H,5H-imidazo[1,2-a]pyrimidin-5-one as a residue (interm. 5).

(b) A mixture of 15.2 parts of interm. 5, 32.4 parts of thionyl chloride and 300 parts of trichloromethane was stirred for 2 hours at reflux temperature. The reaction mixture was evaporated and the residue was treated with 40 parts of acetonitrile. The product was filtered off and dried, yielding 13.2 parts (69.5%) of 6-(2-chloroethyl)-2,3-dihydro-1,7-dimethyl-1H,5H-imidazo[1,2-a]pyrimidin-5-one monohydrochloride; mp. 220° C. (interm. 6).

EXAMPLE 3

(a) A mixture of 43 parts of benzenemethanamine and 77 parts of interm. 1 was stirred for 5 hours in an oil bath at 150°-160° C. After cooling, the precipitated product was stirred in water. The product was filtered off, washed twice with water and crystallized from ethanol, yielding 78 parts (79%) of 5-(2-hydroxyethyl)-6-methyl-2-[(phenylmethyl)-amino]-4(3H)-pyrimidinone; mp. 187.3° C. (interm. 7).

(b) To a stirred suspension of 137 parts of interm. 7 in 564 parts of iodomethane were added 90 parts of N/-dimethylformamide. The mixture was stirred for 30 minutes at room temperature and 71 parts of a sodium methoxide solution 30% were added (exothermic reaction, the temperature rose from 22° C.→40° C.). The reaction mixture was stirred for 2 hours. The reaction mixture was evaporated under reduced pressure and the residue was treated with 1000 parts of water. The solid product was filtered off and crystallized twice: first from 80 parts of acetonitrile and then from 640 parts of acetonitrile. After cooling to 0° C., the product was filtered off and dried, yielding 81.4 parts (59.6%) of 5-(2-hydroxy-ethyl)-3,6-dimethyl-2-[(phenylmethyl)amino]-4(3H)-pyrimidinone (interm. 8).

Following the procedure described in example 2b hereinabove, intermediate 8 was converted into 5-(2-chloroethyl)-3,6-dimethyl-2-[(phenylmethyl)amino]-4(3H)-pyrimidinone monohydrochloride (interm. 9).

EXAMPLE 4

To a stirred mixture of 67.7 parts of 2-amino-5-(2-hydroxyethyl)-6-methyl-4(3H)-pyrimidinone and 800 parts of ethanol were added 80 parts of a sodium methoxide solution 30%. The reaction mixture was heated to reflux temperature and 62.5 parts of iodomethane were added dropwise. Upon complete addition, stirring was continued for 4 hours at reflux temperature. The reaction mixture was evaporated and the residue was suspended in 400 parts of water. The precipitated product was filtered off, washed with 40 parts of ethanol and dried, yielding 58.3 parts (79.6%) of 2-amino-5-(2-hydroxyethyl)-3,6-dimethyl-4(3H)-pyrimidinone (interm. 10).

Following the procedure described in example 2b hereinabove, intermediate 10 was converted into 2-amino-5-(2-chloroethyl)-3,6-dimethyl-4(3H)-pyrimidinone monohydrochloride (interm. 11).

EXAMPLE 5

(a) A mixture of 200 parts of 2-amino-3-(2-hydroxyethyl)-3,6-dimethyl-4(3H)-pyrimidinone, 210 parts of acetic acid and 1350 parts of acetic acid anhydride was stirred for 5 hours at reflux temperature. After cooling, the reaction mixture was evaporated in vacuo and the residue was solidified while stirring in a mixture of ethyl acetate and 2,2'-oxybispropane (1:1 by volume). The solid product was filtered off (the filtrate was set aside), washed with 2,2'-oxybispropane and dried, yielding a first fraction of 134 parts (45.9%) of 2-(acetylamino)-1,2-dihydro-1,4-dimethyl-6-oxo-5-pyrimidineethanol acetate(ester). The filtrate, which was set aside (see above) was cooled at −10° C. The precipitated product was filtered off and dried, yielding a second fraction of 156 parts (53.4%) of 2-(acetylamino)-1,2-dihydro-1,4-dimethyl-6-oxo-5-pyrimidineethanol acetate(ester). Total yield: 190 parts (99.3%) of 2-(acetylamino)-1,2-dihydro-1,4-dimethyl-6-oxo-5-pyrimidineethanol acetate(ester) (interm. 12).

(b) 19.8 Parts of a sodium hydride dispersion 50% were suspended twice in 64 parts of petroleum ether and the solvent was decanted each time. A sodium hydride dispersion 50% was stirred in 94 parts of N/-dimethylformamide under nitrogen atmosphere. A mixture of 88.2 parts of interm. 12 and 282 parts of N/-dimethylformamide was added dropwise to the previous mixture at <15° C. Upon complete addition, stirring was continued for 30 minutes. 57 Parts of iodomethane were added dropwise at room temperature. The reaction mixture was stirred for 10 minutes at 50° C. After cooling to 10° C., the precipitate was filtered off and the filtrate was evaporated. The residue was taken up in 300 parts of water and 63.5 parts of hydrochloric acid and the whole was stirred for 3 hours at reflux temperature. The whole was evaporated, the residue was taken up in 300 parts of water and treated with ammonium hydroxide. The precipitated product was filtered off, washed with 40 parts of acetonitrile and dried, yielding 35.7 part (54.8%) of 5-(2-hydroxyethyl)-3,6-dimethyl-2-(methylamino)-4(3H)-pyrimidinone (interm. 13).

Following the procedure described in example 2b hereinabove, intermediate 13 was converted into 5-(2-chloroethyl)-3,6-dimethyl-2-(methylamino)-4(3H)-pyrimidinone monohydrochloride (interm. 14).

EXAMPLE 6

80.0 Parts of 1-methyl-1H-imidazol-2-amine monohydrochloride, monohydrate were boiled in 600 parts of phosphoryl chloride. The whole was cooled and the phosphoryl chloride was decanted. The solid residue was heated on a steam bath and 49 parts of methylbenzene were added. After stirring for 30 minutes, 78 parts of 3-acetyl-4,5-dihydro-2(3H)-furanone were added during 20 minutes. Upon completion, stirring was continued for 18 hours. The mixture was quenched by carefully adding 200 parts of water. The mixture was treated with ammonium hydroxide to pH 8. The precipitated product was filtered off, washed with water and crystallized twice from a mixture of dichloromethane, methanol and 1,1'-oxybisethane. The product was filtered off, washed with 1,1'-oxybisethane and dried, yielding 90.2 parts (76.2%) of 6-(2-chloroethyl)-1,7-dimethyl-1H,5H-imidazo[1,2-a]pyrimidin-5-one; mp. 198.2° C. (interm 15).

EXAMPLE 7

(a) To a stirred and cooled (2-propanone-CO$_2$ bath) amount of 35.5 parts of 1-propanamine were added slowly 36 parts of acetic acid, keeping the temperature between −5° C. and 0° C. Next there were added 80.2 parts of intermediate 1 and the mixture was refluxed for 2 hours. After cooling, the reaction mixture was diluted with 300 parts of water and basified with sodium hydroxide. The whole was stirred overnight at room temperature. The product was filtered off, washed with acetonitrile and dried, yielding 63.4 parts (75.0%) of 5-(2-hydroxyethyl)-6-methyl-2-(propylamino)-4(3H)-pyrimidinone (interm. 16).

(b) To a stirred mixture of 63.4 parts of intermediate 16 and 376 parts of N/-dimethylformamide were added 51.0 parts of a solution of sodium methoxide in methanol 30% and, after stirring for ½ hour at room temperature, 42.6 parts of iodomethane. Stirring was continued for 2 hours. The product was filtered off, washed with water (2×) and acetonitrile and dried, yielding 37.6 parts (55.6) of 5-(2-hydroxyethyl)-3,6-dimethyl-2-(propylamino)-4(3H)-pyrimidinone; mp. 240° C. (interm. 17).

(c) To a stirred mixture of 36 parts of intermediate 17 and 373 parts of trichloromethane were added slowly 48.6 parts of thionyl chloride. After refluxing for 2 hours, the reaction mixture was evaporated. The residue was diluted with 300 parts of water and the whole was basified with sodium hydroxide. The solid was filtered off and dissolved in trichloromethane. This solution was dried, filtered and evaporated and the residue was triturated with acetonitrile. The product was filtered off at 0° C. and dried, yielding 34.8 parts (89.2%) of 5-(2-chloroethyl)-3,6-dimethyl-2-(propylamino)-4(3H)-pyrimidinone; mp. 150° C. (interm. 18). In a similar manner intermediate 1 was also converted into: 2-(butylamino)-5-(2-chloroethyl)-3,6-dimethyl-4(3H)pyrimidinone; mp. 115° C. (interm. 19); 5-(2-chloroethyl)-2-(ethylamino)-3,6-dimethyl-4(3H)-pyrimidinone; mp. 160° C. (interm. 20)

EXAMPLE 8

(a) A mixture of 20 parts of 2-pyridinemethanamine, 37 parts of intermediate 1,200 parts of 1,2-ethanediol and 1.05 parts of acetic acid was stirred for 4 hours at 160° C. After cooling, the mixture was stirred in water, which was slightly basified with ammonium hydroxide.

The whole was extracted with trichloromethane. The aqueous layer was evaporated and the residual oil was stirred with some 2-propanol for 1 hour. The product was filtered off, washed with 2-propanol and dried, yielding 21 parts (44.1%) of 5-(2-hydroxyethyl)-6-methyl-2-[(2-pyridinylmethyl)amino]-4(3H)-pyrimidinone; mp. −185° C. (interm. 21).

(b) A mixture of 21 parts of intermediate 21, 6 parts of potassium hydroxide and 77.1 parts of dimethyl sulfoxide was stirred for 1 hour at 70° C. After cooling to 10° C., there were added dropwise 14 parts of iodomethane. Stirring was continued overnight and then the reaction mixture was diluted with 600 parts of water, while stirring. The solid was filtered off, washed with water and dissolved in trichloromethane. This solution was dried, filtered and evaporated and the residue was crystallized from a mixture of 4-methyl-2-pentanone and 2,2′-oxybispropane. The product was filtered off and dried, yielding 11.5 parts (52.4%) of 5-(2-hydroxyethyl)-3,6-dimethyl-2-[(2-pyridinylmethyl)amino]-4(3H)-pyrimidinone; mp. 245° C. (interm. 22).

(c) To a stirred mixture of 11 parts of intermediate 22 and 298 parts of trichloromethane were added dropwise 20 parts of thionyl chloride. Stirring was continued for 1 hour at reflux temperature. After cooling, the reaction mixture was evaporated and the residue was stirred in acetonitrile at 35° C. The product was filtered off and dried, yielding 11 parts (75.2%) of 5-(2-chloroethyl)-3,6-dimethyl-2-[(2-pyridinylmethyl)amino]-4(3H)-pyrimidinone dihydrochloride (interm. 23).

EXAMPLE 9

(a) A mixture of 40 parts of intermediate 1, 18.75 parts of 2-ethoxyethanamine and 186 parts of 2-ethoxyethanol was stirred for 5 hours at reflux temperature under a nitrogen atmosphere. (The methanethiol set free during the course of the reaction, was absorbed in a sodium hypochlorite solution.) The reaction mixture was evaporated and the residue was crystallized from acetonitrile. The product was filtered off and dried, yielding 35.2 parts (72.9%) of 2-[(2-ethoxyethyl)amino]-5-(2-hydroxyethyl)-6-methyl-4(3H)-pyrimidinone. The mother liquor was evaporated and the residue was purified by column chromatography (silica gel; CH$_2$Cl$_2$/CH$_3$OH 90:10). The eluent of the desired fraction was evaporated and the residue was crystallized from acetonitrile, yielding an additional 4.6 parts (9.5%) of 2-[(2-ethoxyethyl)amino]-5-(2-hydroxyethyl)-6-methyl-4(3H)-pyrimidinone. Total yield: 39.8 parts (82.4%); mp. 172.4° C. (interm. 24).

(b) To a suspension of 65.6 parts of intermediate 24 in 310 parts of N/ -dimethylformamide were added 48.1 parts of a sodium methoxide solution in methanol 30% and, after stirring for 15 min., 40.1 parts of iodomethane. Stirring was continued for 4 hours. After cooling, the precipitate was filtered off and crystallized from acetonitrile. The product was filtered off and dried, yielding 55.5 parts (79.9%) of 2-[(2-ethoxyethyl)amino]-5-(2-hydroxyethyl)-3,6-dimethyl-4(3H)-pyrimidinone; mp. 194.5° C. (interm. 25).

(c) A mixture of 19 parts of intermediate 25, 27.5 parts of thionyl chloride and 253 parts of trichloromethane was stirred for 3 hours at reflux temperature and was then evaporated. The residue was co-evaporated with methylbenzene and subsequently crystallized from 2-propanol. The product was filtered off and dried, yielding 16.36 parts (71.3%) of 5-(2-chloroethyl)-2-[(2-ethoxyethyl)amino]-3,6-dimethyl-4(3H)-pyrimidinone monohydrochloride (interm. 26).

In a similar manner there was also prepared 3,4-dihydro-3,6-dimethyl-2-[[(5-methyl-2-furanyl)methyl]amino]-4-oxo-5-pyrimidineethanol methanesulfonate(ester) (interm. 27).

EXAMPLE 10

(a) A mixture of 80 parts of intermediate 1, 23 parts of methylhydrazine and 372 parts of 2-ethoxyethanol was stirred for 7 hours at reflux temperature and for 8 hours at room temperature. After cooling to 0° C., the product was filtered off, washed with acetonitrile (2×) and dried, yielding 65 parts (82.0%) of 5-(2-hydroxyethyl)-6-methyl-2-(1-methylhydrazino)-4(3H)-pyrimidinone; mp. 180° C. (interm. 28).

(b) To a stirred and heated (40° C.) mixture of 63.4 parts of intermediate 28, 38.2 parts of sodium carbonate and 470 parts of N/ -dimethylformamide were added slowly 33.3 parts of 1-chloropropanone. Stirring was continued for 4 hours at 110° C. and for 8 hours at room temperature. The reaction mixture was filtered and the filtrate was evaporated. The residue was triturated with acetonitrile. The product was filtered off, washed with acetonitrile (2×) and dried, yielding 38 parts (50.3%) of 1,4-dihydro-7-(2-hydroxyethyl)-1,3,8-trimethyl-6H-pyrimido[2,1-c][1,2,4]triazin-6-one; mp. 140° C. (interm. 29).

(c) To a stirred mixture of 2.35 parts of intermediate 29 and 74.5 parts of trichloromethane were added 4.9 parts of thionyl chloride. After refluxing for 2 hours, the reaction mixture was evaporated and the residue was triturated with acetonitrile. The product was filtered off and dried, yielding 2.5 parts (98.1%) of 7-(2-chloroethyl)-1,4-dihydro-1,3,8-trimethyl-6H-pyrimido[2,1-c][1,2,4]triazin-6-one; mp. 180° C. (interm. 30).

EXAMPLE 11

(a) To a stirred mixture of 9.9 parts of intermediate 28, 7.41 parts of triethoxymethane and 94 parts of N/ -dimethylformamide were added 3 drops of formic acid. Stirring was continued overnight at 100° C. and for 3 hours at 140° C. The reaction mixture was evaporated and the residue was triturated with acetonitrile. The product was filtered off and dried, yielding 6.8 parts (65.3%) of 6-(2-hydroxyethyl)-1,7-dimethyl-1,2,4-triazolo[4,3-a]-pyrimidin-5(1H)-one; mp. 215° C. (interm. 31).

(b) To a stirred mixture of 29.7 parts of intermediate 28, 376 parts of N/ -dimethylformamide and 5 drops of formic acid were added 27.6 parts of triethoxyethane. The mixture was refluxed for 5 hours and was then evaporated. The residue was triturated with acetonitrile. The product was filtered off and dried, yielding 26.0 parts (78.0%) of 6-(2-hydroxyethyl)-1,3,7-trimethyl-1,2,4-triazolo[4,3-a]pyrimidin-5(1H)-one; mp. 170° C. (interm. 32).

(c) To a stirred solution of 25 parts of intermediate 32 in 596 parts of trichloromethane were added slowly 32.4 parts of thionyl chloride. The mixture was refluxed for 2 hours and was then evaporated. The residue was triturated in acetonitrile. The product was filtered off and dried, yielding 12.5 parts (47.2%) of 6-(2-chloroethyl)-1,3,7-trimethyl-1,2,4-triazolo[4,3-a]pyrimidin-5(1H)-one. The filtrate was evaporated and the residue was stirred for 1 hour in a mixture of 100 parts of water and 27 parts of ammonium hydroxide. The product was filtered off, washed with ethanol and 2,2'-oxybispropane and dried, yielding 9.2 parts (34.7%) of 6-(2-chloroethyl)-1,3,7-trimethyl-1,2,4-triazolo[4,3-a]pyrimidin-5(1H)-one. Total yield: 21.7 parts (81.9%); mp. 140° C. (interm. 33).

B. Preparation of Final Compounds

EXAMPLE 12

(a) A mixture of 11.9 parts of interm. 11, 14.5 parts of 1-[(4-fluorophenyl)methyl]-2-(4-piperidinylmethyl)-1H-benzimidazole (prepared as described in Example 26 of U.S. Pat. No. 4,695,575), 12.72 parts of sodium carbonate and 400 parts of 4-methyl-2-pentanone was stirred for 42 hours at reflux temperature. After cooling, water was added to the mixture and the whole was stirred for 20 minutes. The precipitate was filtered off, crystallized from ethanol and filtered. This filtrate was combined with the 4-methyl-2-pentanone filtrate and evaporated. The residue was purified by column chromatography over silica gel using a mixture of dichloromethane and methanol (95:5 by volume) as eluent. The pure fractions were collected and the eluent was evaporated. The residue was crystallized twice from acetonitrile and a few drops of water. The crystallized product was filtered off, washed with 2,2'-oxybispropane and dried, yielding 11.25 parts (51.2%) of 2-amino-5-[2-[4-[[1-[(4-fluorophenyl)methyl]-1H-benzimidazol-2-yl]-methyl]-1-piperidinyl]ethyl]-3,6-dimethyl-4(3H)pyrimidinone; mp. 146.6° C. (compound 11).

(b) A solution of 3.66 parts of compound 11 and 0.82 parts of isocyanatobenzene in 135 parts of tetrahydrofuran was stirred for 5 hours at reflux temperature. The reaction mixture was evaporated and the residue was purified by column chromatography over silica gel using a mixture of dichloromethane and methanol (90:10 by volume) as eluent. The pure fractions were collected and the eluent was evaporated. The residue was crystallized from acetonitrile. The product was filtered off and dried, yielding 2.38 parts (52.2%) of N-[5-[2-[4-[[1-[(4-fluorophenyl)methyl]-1H-benzimidazol-2-yl]methyl]-1-piperidinyl]-ethyl]-3,4-dihydro-3,6-dimethyl-4-oxo-2-pyrimidinyl]-N'-phenylurea; mp. 156.9° C. (compound 13).

EXAMPLE 13

A mixture of 11.3 parts of 6-(2-chloroethyl)-1,7-dimethylimidazo[1,2-a]pyrimidin-5(1H)-one (interm. 15), 18.9 parts of N-(4-piperidinyl)-1H-benzimidazol-2-amine dihydrobromide, 16 parts of sodium carbonate, 0.01 parts of potassium iodide and 376 parts of N/-dimethylacetamide was stirred overnight at 70° C. The reaction mixture was filtered and the filtrate was evaporated. The residue was taken up in a mixture of water, dichloromethane and methanol. The organic layer was separated and the aqueous layer was re-extracted with a mixture of dichloromethane and methanol. The combined organic layers were dried, filtered and evaporated. The residue was crystallized from ethanol, yielding 17.5 parts (86.3%) of 6-[2-[4-(1H-benzimidazol-2-ylamino)-1-piperidinyl]-ethyl]-1,7-dimethylimidazo[1,2-a]pyrimidin-5(1H)-one; mp. 229.5° C. (comp. 80).

EXAMPLE 14

(a) To a stirred amount of 282 parts of N/-dimethylformamide were added portionwise 2.6 parts of a dispersion of sodium hydride in mineral oil (50%) and 12.2 parts of compound 80 under a nitrogen atmosphere. After stirring for 1 hour at room temperature, there was added dropwise a solution of 6.1 parts of ethyl 4-chloromethyl-5-methyl-2-furancarboxylate in a small amount of N/-dimethylformamide. Stirring at room temperature was continued for 3 hours. The reaction mixture was poured into a mixture of water, sodium hydrogen carbonate and dichloromethane. The precipitate was filtered off and crystallized from acetonitrile, yielding 15.5 parts (89.0%) of ethyl 4-[[2-[[1-[2-(1,5-dihydro-1,7-dimethyl-5-oxoimidazo[1,2-a]pyrimidin-6-yl)ethyl]-4-piperidinyl]amino]-1H-benzimidazol-1-yl]methyl]-5-methyl-2-furancarboxylate hemihydrate; mp. 150° C. (interm. 34).

(b) To a stirred amount of 134 parts of tetrahydrofuran were added portionwise 0.24 parts of lithium aluminum hydride under a nitrogen atmosphere. Next there was added dropwise a solution of 3.5 parts of intermediate 34 in a small amount of tetrahydrofuran. After refluxing for 1 hour and subsequent cooling, there were added 0.5 parts of water, 0.58 parts of sodium hydroxide 15% and 0.5 parts of water. The mixture was filtered and the filtrate was evaporated. The residue was purified by column chromatography (silica gel; $CH_2Cl_2/CH_3OH/CH_3OH(NH_3)$ 95:5:1). The eluent of the desired fraction was evaporated and the residue was crystallized from a mixture of acetonitrile and ethanol. The product was filtered off and dried, yielding 1.3 parts (38.9%) of 6-[2-[4-[[1-[[5-(hydroxymethyl)-2-methyl-3-furanyl]methyl]-1H-benzimidazol-2-yl]amino]-1-piperidinyl]ethyl]-1,7-dimethylimidazo[1,2-a]pyrimidin-5(1H)-one monohydrate; mp. 223.4° C. (comp. 81).

All other compounds listed in tables 1 and 2 were prepared following the procedures described hereinabove.

TABLE 1

| Comp. No. | Ex. No. | R | B | $A^1$ | $R^1$ | Physical Data (mp.) |
|---|---|---|---|---|---|---|
| 1 | 12 | $CH_3$— | NH | CH | 4-F—$C_6H_4$—$CH_2$— | 182.7° C./$H_2O$ |
| 2 | 12 | $CH_3$— | NH | N | 5-methyl-2-furanylmethyl | 185.3° C. |
| 3 | 12 | $C_6H_5$—$CH_2$— | NH | N | 5-methyl-2-furanylmethyl | 186.9° C./2 $H_2O$/* |
| 4 | 12 | $C_6H_5$—$CH_2$— | NH | N | 2-ethoxyethyl | 182.1° C./2 $H_2O$/* |
| 5 | 12 | H— | NH | N | 2-ethoxyethyl | 219.7° C. |
| 6 | 12 | $C_6H_5NHCO$— | NH | N | 2-ethoxyethyl | 147.1° C./$H_2O$ |
| 7 | 12 | H— | NH | CH | 4-F—$C_6H_4$—$CH_2$— | 199.7° C./$H_2O$ |

TABLE 1-continued

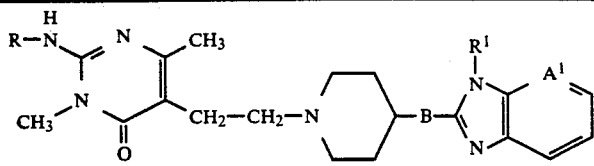

| Comp. No. | Ex. No. | R | B | $A^1$ | $R^1$ | Physical Data (mp.) |
|---|---|---|---|---|---|---|
| 8 | 12 | $CH_3NHCO-$ | NH | CH | $4-F-C_6H_4-CH_2-$ | 140.9° C. |
| 9 | 12 | $C_6H_5NHCO-$ | NH | CH | $4-F-C_6H_4-CH_2-$ | 171.3° C. |
| 10 | 12 | H— | NH | N | 5-methyl-2-furanylmethyl | 197.4° C. |
| 11 | 12 | H— | $CH_2$ | CH | $4-F-C_6H_4-CH_2-$ | 146.6° C. |
| 12 | 12 | $CH_3NHCO-$ | NH | N | 5-methyl-2-furanylmethyl | 163.4° C. |
| 13 | 12 | $C_6H_5NHCO-$ | $CH_2$ | CH | $4-F-C_6H_4-CH_2-$ | 156.9° C. |
| 14 | 12 | $CH_3NHCO-$ | NH | N | 2-ethoxyethyl | 177.6° C. |
| 15 | 12 | H— | NH | CH | 5-hydroxymethyl-2-furanylmethyl | 227.2° C. |
| 16 | 12 | H— | NH | N | 5-hydroxymethyl-2-furanylmethyl | 195° C./0.5 $H_2O$ |
| 17 | 12 | $CH_3$ | NH | CH | 5-hydroxymethyl-2-furanylmethyl | 204.7° C. |
| 18 | 12 | $CH_3$ | NH | N | 5-hydroxymethyl-2-furanylmethyl | 195.8° C. |
| 19 | 12 | 2-pyridinylmethyl | NH | N | 5-methyl-2-furanylmethyl | 100.2° C./0.5 $H_2O$ |
| 20 | 12 | 2-pyridinylmethyl | NH | CH | $4-F-C_6H_4-CH_2-$ | 176.2° C. |
| 21 | 12 | 2-pyridinylmethyl | $CH_2$ | CH | $4-F-C_6H_4-CH_2-$ | 178.5° C. |
| 22 | 12 | $n-C_4H_9-$ | NH | N | 2-ethoxyethyl | 200° C./$H_2O$/2* |
| 23 | 12 | 2-pyridinylmethyl | NH | N | 2-ethoxyethyl | 155.9° C./½$H_2O$/2.5* |
| 24 | 12 | $C_2H_5-$ | NH | N | 2-ethoxyethyl | 193.5° C./$H_2O$/2* |
| 25 | 12 | 2-ethoxyethyl | NH | CH | $4-F-C_6H_4-CH_2-$ | 160.6° C. |
| 26 | 12 | $C_2H_5-$ | NH | CH | $4-F-C_6H_4-CH_2-$ | 132.5° C./0.5 $H_2O$ |
| 27 | 12 | $n-C_4H_9-$ | NH | CH | $4-F-C_6H_4-CH_2-$ | 187.2° C. |
| 28 | 12 | $C_6H_5-NHCO-$ | NH | N | 5-methyl-2-furanylmethyl | 118.7° C. |
| 29 | 12 | $C_2H_5-$ | NH | CH | 5-hydroxymethyl-2-furanylmethyl | 201.3° C. |
| 30 | 12 | 2-ethoxyethyl | NH | CH | 5-hydroxymethyl-2-furanylmethyl | 150.1° C. |
| 31 | 12 | $C_2H_5-$ | NH | N | 5-hydroxymethyl-2-furanylmethyl | 190.6° C. |
| 32 | 12 | 2-ethoxyethyl | $CH_2$ | CH | $4-F-C_6H_4-CH_2-$ | 143.4° C. |
| 33 | 12 | 2-ethoxyethyl | NH | CH | 5-hydroxymethyl-2-furanylmethyl | 95.2° C./0.5 $H_2O$ |
| 34 | 12 | $n-C_4H_9-$ | NH | N | 5-methyl-2-furanylmethyl | 215.0° C./2* |
| 35 | 12 | $n-C_4H_9-$ | $CH_2$ | CH | $4-F-C_6H_4-CH_2-$ | 103.0° C. |
| 36 | 12 | $n-C_3H_7-$ | NH | N | 2-ethoxyethyl | 128.6° C. |
| 37 | 12 | $n-C_3H_7-$ | NH | N | 5-methyl-2-furanylmethyl | 100.3° C./0.5 $H_2O$ |
| 38 | 12 | $n-C_3H_7-$ | NH | CH | $4-F-C_6H_4-CH_2-$ | 131.7° C./0.5 $H_2O$ |
| 39 | 12 | 2-pyridinylmethyl | NH | CH | 5-hydroxymethyl-2-furanylmethyl | 215.9° C. |
| 40 | 12 | $n-C_4H_9-$ | NH | CH | 5-hydroxymethyl-2-furanylmethyl | 180.2° C./0.5 $H_2O$ |
| 41 | 12 | $n-C_3H_7-$ | $CH_2$ | CH | $4-F-C_6H_4-CH_2-$ | 185.6° C./2* |
| 42 | 12 | 5-methyl-2-furanylmethyl | $CH_2$ | CH | $4-F-C_6H_4-CH_2-$ | 127.5° C. |
| 43 | 12 | $n-C_3H_7$ | NH | CH | 5-hydroxymethyl-2-furanylmethyl | 192.9° C./0.5 $H_2O$ |
| 44 | 12 | 5-methyl-2-furanylmethyl | NH | N | 5-hydroxymethyl-2-furanylmethyl | 150.1° C. |
| 45 | 12 | 5-methyl-2-furanylmethyl | NH | CH | 5-hydroxymethyl-2-furanylmethyl | 139.4° C./0.5 $H_2O$ |
| 46 | 12 | $CH_3-$ | NH | N | 2-ethoxyethyl | 174.7° C. |
| 47 | 12 | H— | $CH_2$ | N | 5-hydroxymethyl-2-furanylmethyl | 195.2° C./0.5 $H_2O$ |

*$(COOH)_2$

TABLE 2

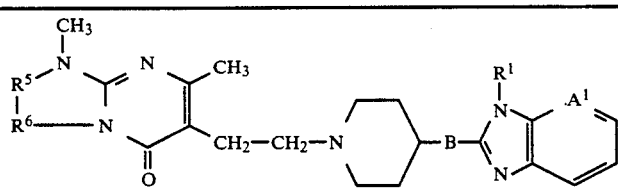

| Comp. No. | Ex. No. | $R^5-R^6$ | B | $A^1$ | $R^1$ | Physical Data (mp.) |
|---|---|---|---|---|---|---|
| 48 | 12 | $-CH=CH-$ | NH | N | 2-ethoxyethyl | 190° C./0.5$H_2O$/* |
| 49 | 12 | $-C(CH_3)=CH-$ | NH | N | 5-methyl-2-furanylmethyl | 209.2° C. |
| 50 | 12 | $-C(CH_3)=CH-$ | $CH_2$ | CH | $4-F-C_6H_4-CH_2$ | 189.5° C. |
| 51 | 12 | $-CH=CH-$ | NH | CH | $4-F-C_6H_4-CH_2$ | 218.5° C. |
| 52 | 12 | $-C(CH_3)=CH-$ | NH | CH | $4-F-C_6H_4-CH_2$ | 212.1° C. |
| 53 | 12 | $-CH=CH-$ | $CH_2$ | CH | $4-F-C_6H_4-CH_2$ | 206° C./$H_2O$/* |
| 54 | 12 | $-CH=CH-$ | NH | N | 5-methyl-2-furanylmethyl | 0.5$H_2O$/* |
| 55 | 12 | $-CH_2-CH_2-$ | NH | CH | $4-F-C_6H_4-CH_2$ | 198° C. |
| 56 | 12 | $-C(CH_3)=CH-$ | NH | N | 2-ethoxyethyl | 151.6° C. |
| 57 | 12 | $-CH_2-CH_2-$ | NH | N | 5-methyl-2-furanylmethyl | 160.2° C. |
| 58 | 12 | $-N=C(CH_3)-CH_2-$ | $CH_2$ | CH | $4-F-C_6H_4-CH_2$ | 137.6° C. |
| 59 | 12 | $-N=C(CH_3)-$ | NH | CH | $4-F-C_6H_4-CH_2$ | 165.0° C. |
| 60 | 12 | $-N=C(CH_3)-$ | $CH_2$ | CH | $4-F-C_6H_4-CH_2$ | 166.4° C. |
| 61 | 12 | $-N=C(CH_3)-CH_2-$ | NH | CH | $4-F-C_6H_4-CH_2$ | 150.1° C. |
| 62 | 12 | $-N=C(CH_3)-CH_2-$ | NH | N | 5-methyl-2-furanylmethyl | 171.5° C. |

TABLE 2-continued

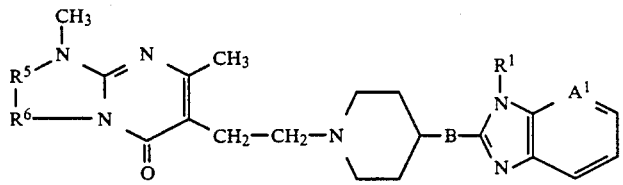

| Comp. No. | Ex. No. | $R^5$—$R^6$ | B | $A^1$ | $R^1$ | Physical Data (mp.) |
|---|---|---|---|---|---|---|
| 63 | 12 | —CH$_2$—CH$_2$— | NH | N | 2-ethoxyethyl | 189.2° C./½H$_2$O/2* |
| 64 | 12 | —N=C(CH$_3$)— | NH | N | 2-ethoxyethyl | 211.2° C./2* |
| 65 | 12 | —N=C(CH$_3$)—CH$_2$— | NH | N | 2-ethoxyethyl | 143.6° C. |
| 66 | 12 | —N=C(CH$_3$)— | NH | CH | 5-hydroxymethyl-2-furanylmethyl | 224.2° C. |
| 67 | 12 | —N=C(CH$_3$)— | NH | N | 5-methyl-2-furanylmethyl | 177.3° C. |
| 68 | 12 | —CH=CH— | NH | CH | 5-hydroxymethyl-2-furanylmethyl | 207.2° C. |
| 69 | 12 | —N=C(CH$_3$)—CH$_2$— | NH | CH | 5-hydroxymethyl-2-furanylmethyl | 227.9° C. |
| 70 | 12 | —CH=CH— | NH | N | 5-hydroxymethyl-2-furanylmethyl | 214.0° C. |
| 71 | 12 | —C(CH$_3$)=CH— | NH | CH | 5-hydroxymethyl-2-furanylmethyl | 272.4° C. |
| 72 | 12 | —N=C(CH$_3$)—CH$_2$— | NH | N | 5-hydroxymethyl-2-furanylmethyl | 187.7° C. |
| 73 | 12 | —N=C(CH$_3$)—CH$_2$— | CH$_2$ | N | 5-hydroxymethyl-2-furanylmethyl | 184.2° C. |
| 74 | 12 | —N=C(CH$_3$)— | CH$_2$ | N | 5-hydroxymethyl-2-furanylmethyl | 165.4° C./H$_2$O |
| 75 | 12 | —CH$_2$—CH$_2$— | CH$_2$ | N | 5-hydroxymethyl-2-furanylmethyl | 102.7° C./H$_2$O |
| 76 | 12 | —CH$_2$—CH$_2$— | CH$_2$ | CH | 5-hydroxymethyl-2-furanylmethyl | 85.8° C./0.5H$_2$O |
| 77 | 12 | —N=C(CH$_3$)—CH$_2$— | CH$_2$ | CH | 5-hydroxymethyl-2-furanylmethyl | 196.7° C. |
| 78 | 12 | —C(CH$_3$)=CH— | CH$_2$ | N | 5-hydroxymethyl-2-furanylmethyl | 195.9° C./1.5H$_2$O |
| 79 | 12 | —CH=CH— | CH$_2$ | CH | 5-hydroxymethyl-2-furanylmethyl | 216.6° C. |
| 80 | 13 | —CH=CH— | NH | CH | H | 229.5° C. |
| 81 | 14 | —CH=CH— | NH | CH | 5-hydroxymethyl-2-furanylmethyl | 223.4° C./H$_2$O |
| 82 | 12 | —N=C(CH$_3$)— | NH | CH | 4-Cl—C$_6$H$_4$—CH$_2$ | 165.5° C. |
| 83 | 12 | —N=C(CH$_3$)— | NH | N | 3-furanylmethyl | 110.1° C./0.5H$_2$O |
| 84 | 12 | —N=C(CH$_3$)— | NH | N | 2-pyridinylmethyl | 192.4° C. |
| 85 | 12 | —N=C(CH$_3$)— | S | N | 4-F—C$_6$H$_4$—CH$_2$ | 156.7° C. |
| 86 | 12 | —N=C(CH$_3$)— | O | N | 4-F—C$_6$H$_4$—CH$_2$ | 137.6° C. |
| 87 | 12 | —N=C(CH$_3$)— | NH | CH | 4-thiazolylmethyl | 158.9° C./H$_2$O |
| 88 | 12 | —N=C(CH$_3$)— | CH$_2$ | CH | 3-furanylmethyl | 117.4° C./0.5H$_2$O |

*(COOH)$_2$

TABLE 3

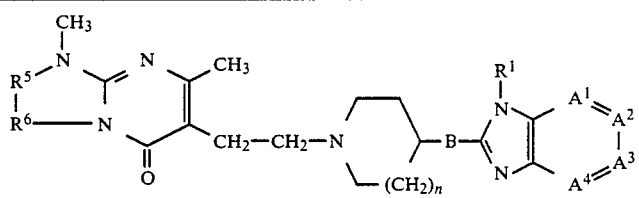

| Comp. No. | Ex. No. | $R^5$—$R^6$ | n | B | —$A^1$=$A^2$—$A^3$=$A^4$— | $R^1$ | Physical Data (mp.) |
|---|---|---|---|---|---|---|---|
| 89 | 12 | —N=C(CH$_3$)— | 0 | NH | —N=CH—CH=CH— | 5-methyl-2-furanylmethyl | 201.2° C./1.5** |
| 90 | 12 | —N=C(CH$_3$)— | 1 | NH | —CH=CH—C(CH$_3$)=CH— | 4-F—C$_6$H$_4$—CH$_2$ | 215.5° C./2** |
| 91 | 12 | —C(CH$_3$)=CH— | 2 | NH | —N=CH—CH=CH— | 5-methyl-2-furanylmethyl | 196.2° C./2** |
| 92 | 12 | —N=C(CH$_3$)— | 2 | NH | —N=CH—CH=CH— | 5-methyl-2-furanylmethyl | 146° C. |
| 93 | 12 | —N=C(CH$_3$)— | 1 | NH | —C(OH)=N—CH=N— | 4-F—C$_6$H$_4$—CH$_2$ | 273.7° C./0.5H$_2$O |
| 94 | 12 | —N=C(CH$_3$)— | 1 | NH | —CH=N—CH=CH— | 4-F—C$_6$H$_4$—CH$_2$ | |
| 95 | 12 | —N=C(CH$_3$)— | 1 | NH | —CH=CH—N=CH— | 4-F—C$_6$H$_4$—CH$_2$ | |
| 96 | 12 | —N=C(CH$_3$)— | 1 | NH | —CH=CH—CH=N— | 4-F—C$_6$H$_4$—CH$_2$ | 206.4° C. |
| 97 | 12 | —N=C(CH$_3$)— | 1 | NH | —N=CH—N=CH— | 2-thienylmethyl | 216.1° C. |
| 98 | 12 | —N=C(CH$_3$)— | 1 | CH$_2$ | —CH=C(OCH$_3$)—CCl=CH— | 4-F—C$_6$H$_4$—CH$_2$ | 180.2° C. |
| 99 | 12 | —N=C(CH$_3$)— | 1 | CH$_2$ | —N=CH—N=C(CH$_3$)— | 4-F—C$_6$H$_4$—CH$_2$ | |

**fumarate

TABLE 4

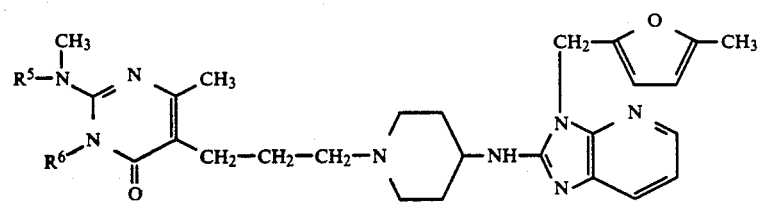

| Comp. No. | Ex. No. | $R^5$ | $R^6$ | Physical Data (mp.) |
|---|---|---|---|---|
| 100 | 12 | H | $CH_3$ | |
| 101 | 12 | —C($CH_3$)=CH— | | |

C. Pharmacological Examples

EXAMPLE 15

The useful antihistaminic properties of the compounds of formula (I) can be demonstrated in the test "Protection of rats from compound 48/80-induced lethality", which is described in U.S. Pat. No. 4,556,660. The $ED_{50}$ values of the tested compounds of formula (I) are listed in the first column of table 4. Said $ED_{50}$ values are the values in mg per kg bodyweight at which the tested compounds protect 50% of the tested animals against compound 48/80-induced lethality.

EXAMPLE 16

The useful antiserotoninergic properties of the compounds of formula (I) can be demonstrated in the test "Protection of rats from compound 48/80-induced gastric lesions", which is described in U.S. Pat. No. 4,556,660. The $ED_{50}$ values of the tested compounds are listed in the second column of table 4. Said $ED_{50}$ values are the doses in mg per kg bodyweight at which the distention of the stomach as well as lesions in the glandular area of the stomach are completely absent in half of the test rats.

EXAMPLE 17

The enhanced peripheral serotoninergic properties of the tested compounds of formula (I) can be demonstrated in the "Combined Apomorphine, tryptamine and norepinephrine test in rats" which is described in Arch. int. Pharmacodyn, 227, 238–253 (1977). Said test provides an empirical evaluation of the relative specificity with which drugs may effect particular neurotransmitters centrally (CNS) as well as peripherally. The tested compounds of formula (I) did not significantly antagonize dopamine, norepinehrine or central serotonin, but were found to be markedly effective peripheral serotonin antagonists as could be observed by the inhibition of tryptamine-induced hyperaemia of the ears in rats. The $ED_{50}$ values of the tested compounds are listed in column 3 of table 4 and represent the dose in mg per kg bodyweight which protects half of the tested animals from peripheral serotonin-induced phenomena, in particular hyperaemia of the ears.

The enhanced serotoninergic properties of the present compounds are clearly evident by comparison with the reference compound 3-[2-[4-[[3-(2-furanylmethyl)-3H-imidazo[4,5-b]pyridin-2-yl]amino]-1-piperidinyl]ethyl]-2-methyl-4H-pyrido[1,2-a]pyrimidin-4-one, which is described in U.S. Pat. No. 4,698,575 and is known generically as barmastine (PINN).

| Comp. No. | 48/80 induced lethality in rats $ED_{50}$ (mg/kg body weight) | 48/80 induced gastric lesions in rats $ED_{50}$ (mg/kg body weight) | tryptamine-induced hyperaemia in rats $ED_{50}$ (mg/kg body weight) |
|---|---|---|---|
| 3 | 0.08 | 0.08 | 0.005 |
| 7 | 0.02 | 0.02 | 0.01 |
| 11 | 0.02 | 0.16 | 0.005 |
| 15 | 0.02 | 0.005 | 0.002 |
| 16 | 0.01 | 0.16 | 0.005 |
| 17 | 0.02 | 0.01 | 0.002 |
| 21 | 0.04 | 0.08 | 0.01 |
| 29 | 0.08 | 0.16 | 0.005 |
| 30 | 0.04 | 0.02 | 0.02 |
| 34 | 0.04 | 0.08 | 0.02 |
| 39 | 0.08 | 0.04 | 0.005 |
| 43 | 0.08 | 0.04 | 0.005 |
| 50 | 0.04 | 0.16 | 0.02 |
| 58 | 0.04 | 0.16 | 0.02 |
| 67 | 0.04 | 0.08 | 0.08 |
| 68 | 0.04 | 0.04 | 0.04 |
| 71 | 0.04 | 0.04 | 0.01 |
| 79 | 0.02 | 0.04 | 0.02 |
| reference | 0.08 | 0.63 | 0.63 |

(D) Composition Examples

EXAMPLE 18: oral drops

500 Parts of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 19: oral solution

9 Parts of methyl 4-hydroxybenzoate and 1 part of propyl 4-hydroxybenzoate were dissolved in 4 l of boiling purified water. In 3 l of this solution were dissolved first 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 20: capsules

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently filled into 1000 suitable hardened gelatin capsules, comprising each 20 mg of the active ingredient.

EXAMPLE 21: film-coated tablets

Preparation of tablet core

A mixture of 100 parts of the A.I., 570 parts lactose and 200 parts starch was mixed well and thereafter humidified with a solution of 5 parts sodium dodecyl sulfate and 10 parts polyvinylpyrrolidone (Kollidon-K90®) in about 200 ml of water. The wet powder mixture was sieved, dried and sieved again. Then there was added 100 parts microcrystalline cellulose (Avicel®) and 15 parts hydrogenated vegetable oil (Sterotex®). The whole was mixed well and compressed into tablets, giving 10.000 tablets, each containing 10 mg of the active ingredient.

Coating

To a solution of 10 parts methyl cellulose (Methocel 60 HG®) in 75 ml of denaturated ethanol there was added a solution of 5 parts of ethyl cellulose (Ethocel 22 cps®) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to the former and then there were added 2.5 parts of magnesium octadecanoate, 5 parts of polyvinylpyrrolidone and 30 ml of concentrated colour suspension (Opaspray K-1-2109®) and the whole was homogenated. The tablet cores were coated with the thus obtained mixture in a coating apparatus.

EXAMPLE 22: injectable solution 1.8 Parts methyl 4-hydroxybenzoate and 0.2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 23: suppositories

3 Parts A.I. was dissolved in a solution of 3 parts 2,3-dihydroxybutanedioic acid in 25 ml polyethylene glycol 400. 12 Parts surfactant (SPAN®) and triglycerides (Witepsol 555®) q.s. ad 300 parts were molten together. The latter mixture was mixed well with the former solution. The thus obtained mixture was poured into moulds at a temperature of 37°-38° C. to form 100 suppositories each containing 30 mg/ml of the A.I.

We claim:

1. A chemical compound having the formula

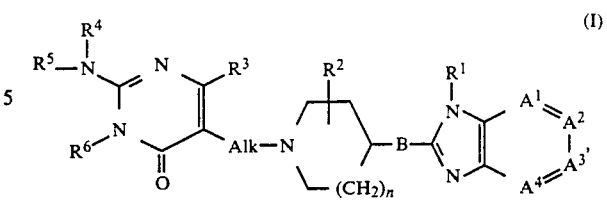

a pharmaceutically acceptable addition salt thereof, and a stereochemically isomeric form thereof, wherein —A$^1$=A$^2$—A$^3$=A$^4$— is a bivalent radical having the formula

| | |
|---|---|
| —CH=CH—CH=CH—, | (a-1) |
| —N=CH—CH=CH—, | (a-2) |
| —CH=N—CH=CH—, | (a-3) |
| —CH=CH—N=CH—, | (a-4) |
| —CH=CH—CH=N—, | (a-5) |
| —N=CH—N=CH— or | (a-6) |
| —CH=N—CH=N—, | (a-7) | wherein one or two hydrogen atoms of said radicals (a-1) to (a-7) each independently from one another may be replaced by halo, $C_{1-6}$alkyl, $C_{1-6}$alkyloxy, hydroxy or trifluoromethyl;

$R^1$ is hydrogen, $C_{1-10}$alkyl, $C_{3-6}$cycloalkyl, Ar$^1$, mono- and di(Ar$^1$)-$C_{1-6}$alkyl, or a radical of formula —Alk—G—R$^7$; wherein G is O or S; and $R^7$ is hydrogen; $C_{2-6}$alkenyl optionally substituted with Ar$^2$; $C_{3-6}$alkynyl; $C_{1-6}$alkyl optionally substituted with Ar$^1$, hydroxy, $C_{1-6}$alkyloxy, carboxyl or $C_{1-6}$alkyloxycarbonyl;

B is NR$^8$, CH$_2$, O, S, SO or SO$_2$; said R$^8$ being hydrogen, $C_{1-6}$alkyl, $C_{3-6}$cycloalkyl, $C_{1-6}$alkylcarbonyl, $C_{1-6}$alkyloxycarbonyl or Ar$^2$-$C_{1-6}$alkyl;

$R^2$ is hydrogen or $C_{1-6}$alkyl;

n is 0, 1 or 2;

each Alk independently is $C_{1-6}$alkanediyl;

$R^3$ is hydrogen or $C_{1-6}$alkyl;

$R^4$ is hydrogen, $C_{1-6}$alkyl optionally substituted with Ar$^2$, pyridinyl, furanyl, 5-methyl-2-furanyl or $C_{1-6}$alkyloxy;

$R^5$ is hydrogen, $C_{1-6}$alkyl, $C_{1-6}$alkylaminocarbonyl or Ar$^2$-aminocarbonyl;

$R^6$ is hydrogen or $C_{1-6}$alkyl; or $R^5$ and $R^6$ taken together may form a bivalent radical of formula

| | |
|---|---|
| —CH$_2$—CH$_2$—, | (b-1) |
| —CH$_2$—CH$_2$—CH$_2$—, | (b-2) |
| —CH=CH—, | (b-3) |
| —CH=N—, | (b-4) |
| —N=CH— or | (b-5) |
| —N=CH—CH$_2$—, | (b-6) | wherein one or where possible two hydrogen atoms of said radicals (b-1) to (b-6) each independently from one another may be replaced by $C_{1-6}$alkyl;

Ar$^1$ is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl; thienyl; halothienyl; furanyl optionally substituted with $C_{1-6}$alkyl and/or hydroxy$C_{1-6}$alkyl; pyridinyl; pyrimidinyl; pyrazinyl; thiazolyl; or imidazolyl optionally substituted with $C_{1-6}$alkyl; and $Ar^2$ is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

2. A compound according to claim 1 wherein $R^1$ is hydrogen, $(Ar^1)C_{1-6}$alkyl or $C_{1-6}$alkyloxy$C_{1-6}$alkyl; or B is NH, $CH_2$, O or S; or $R^2$ is hydrogen; or $R^3$ is $C_{1-6}$alkyl; or $R^5$ is hydrogen, $C_{1-6}$alkylaminocarbonyl or phenylaminocarbonyl; or $R^6$ is $C_{1-6}$alkyl; or $R^5$ and $R^6$ taken together may form a bivalent radical of formula (b-1) to (b-6) wherein one hydrogen atom of said radicals (b-1) to (b-6) may be replaced by $C_{1-6}$alkyl; or $Ar^1$ is phenyl optionally substituted with halo; furanyl optionally substituted with $C_{1-6}$alkyl and/or hydroxy$C_{1-6}$alkyl; pyridinyl; or thiazolyl.

3. A compound according to claim 2 wherein $-A^1=A^2-A^3=A^4-$ is a bivalent radical having the formula (a-1) wherein one or two hydrogen atoms each independently from one another may be replaced by halo, $C_{1-4}$alkyl or $C_{1-4}$alkyloxy; (a-2); (a-6) wherein one hydrogen atom may be replaced by $C_{1-4}$alkyl; or (a-7) wherein one hydrogen atom may be replaced by hydroxy; or $R^1$ is hydrogen, $(Ar^1)C_{1-4}$alkyl or $C_{1-4}$alkyloxy$C_{2-4}$alkyl; and/or Alk is 1,2-ethanediyl; or $R^3$ is $C_{1-4}$alkyl; or $R^4$ is hydrogen, $C_{1-6}$alkyl, phenyl$C_{1-4}$alkyl, pyridinyl$C_{1-4}$alkyl, 5-methyl-2-furanyl$C_{1-4}$alkyl or $C_{1-4}$alkyloxy$C_{2-4}$alkyl; or $R^5$ is hydrogen, $C_{1-4}$alkylaminocarbonyl or phenylaminocarbonyl; or $R^6$ is $C_{1-6}$alkyl; or $R^5$ and $R^6$ taken together may form a bivalent radical of formula (b-1); (b-3); (b-5) or (b-6), wherein one hydrogen atom of said radicals (b-3), (b-5) and (b-6) may be replaced by $C_{1-4}$alkyl; or $Ar^1$ is phenyl optionally substituted with halo; furanyl substituted with $C_{1-4}$alkyl and/or hydroxy$C_{1-4}$alkyl; pyridinyl; or thiazolyl.

4. A compound according to claim 3 wherein $-A^1=A^2-A^3=A^4-$ is a bivalent radical having the formula (a-1) or (a-2); or $R^1$ is 4-fluorophenylmethyl; 5-methyl-2-furanylmethyl; 5-hydroxymethyl-2-furanylmethyl or 2-ethoxyethyl;

B is NH or $CH_2$; or n is 1; or $R^3$ is methyl; or $R^4$ is hydrogen, $C_{1-6}$alkyl; phenylmethyl; pyridinylmethyl; 5-methyl-2-furanylmethyl or 2-ethoxyethyl; or $R^5$ is hydrogen, methylaminocarbonyl or phenylaminocarbonyl; or $R^6$ is $C_{1-6}$alkyl; or $R^5$ and $R^6$ taken together may form a bivalent radical of formula (b-3) or (b-6) wherein one hydrogen atom of said bivalent radicals may be replaced by methyl.

5. A compound according to claim 4 wherein $R^4$ is hydrogen, $C_{1-4}$alkyl, phenylmethyl, 2-pyridinylmethyl or 2-ethoxyethyl; or $R^5$ is hydrogen; or $R^6$ is methyl; or $R^5$ and $R^6$ taken together may form a bivalent radical of formula (b-3) wherein one hydrogen atom of said bivalent radical may be replaced by methyl.

6. A compound according to claim 1 wherein the compound is selected from 2-amino-5-[2-[4-[[1-[[5-(hydroxymethyl)-2-furanyl]methyl]-1H-benzimidazol-2-yl]amino]-1-piperidinyl]ethyl]-3,6-dimethyl-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-(methylamino)-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-[(2-pyridinylmethyl)amino]-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-(propylamino)-4(3H)-pyrimidinone, the pharmaceutically acceptable acid addition salts and the possible stereochemically isomeric forms thereof.

7. An anti-allergic composition comprising an inert carrier and as active ingredient an antiallergically effective amount of a compound as claimed in claim 1.

8. A composition according to claim 7 wherein $R^1$ is hydrogen, $(Ar^1)C_{1-6}$alkyl or $C_{1-6}$alkyloxy$C_{1-6}$alkyl; or B is NH, $CH_2$, O or S; or $R^2$ is hydrogen; or $R^3$ is $C_{1-6}$alkyl; or $R^5$ is hydrogen, $C_{1-6}$alkylaminocarbonyl or phenylaminocarbonyl; or $R^6$ is $C_{1-6}$alkyl; or $R^5$ and $R^6$ taken together may form a bivalent radical of formula (b-1) to (b-6) wherein one hydrogen atom of said radicals (b-1) to (b-6) may be replaced by $C_{1-6}$alkyl; or $Ar^1$ is phenyl optionally substituted with halo; furanyl optionally substituted with $C_{1-6}$alkyl and/or hydroxy$C_{1-6}$alkyl; pyridinyl; or thiazolyl.

9. A composition according to claim 8 wherein $-A^1=A^2-A^3=A^4-$ is a bivalent radical having the formula (a-1) wherein one or two hydrogen atoms each independently from one another may be replaced by halo, $C_{1-4}$alkyl or $C_{1-4}$alkyloxy; (a-2); (a-6) wherein one hydrogen atom may be replaced by $C_{1-4}$alkyl; or (a-7) wherein one hydrogen atom may be replaced by hydroxy; or $R^1$ is hydrogen, $(Ar^1)C_{1-4}$alkyl or $C_{1-4}$alkyloxy$C_{2-4}$alkyl; and/or Alk is 1,2-ethanediyl; or $R^3$ is $C_{1-4}$alkyl; or $R^4$ is hydrogen, $C_{1-6}$alkyl, phenyl$C_{1-4}$alkyl, pyridinyl$C_{1-4}$alkyl, 5-methyl-2-furanyl$C_{1-4}$alkyl or $C_{1-4}$alkyloxy$C_{2-4}$alkyl; or $R^5$ is hydrogen, $C_{1-4}$alkylaminocarbonyl or phenylaminocarbonyl; or $R^6$ is $C_{1-6}$alkyl; or $R^5$ and $R^6$ taken together may form a bivalent radical of formula (b-1); (b-3); (b-5) or (b-6), wherein one hydrogen atom of said radicals (b-3), (b-5) and (b-6) may be replaced by $C_{1-4}$alkyl; or $Ar^1$ is phenyl optionally substituted with halo; furanyl substituted with $C_{1-4}$alkyl and/or hydroxy$C_{1-4}$alkyl; pyridinyl; or thiazolyl.

10. A composition according to claim 9 wherein
—$A^1$=$A^2$—$A^3$=$A^4$— is a bivalent radical having the formula (a-1) or (a-2); or $R^1$ is 4-fluorophenylmethyl; 5-methyl-2-furanylmethyl; 5-hydroxymethyl-2-furanylmethyl or 2-ethoxyethyl;

B is NH or $CH_2$; or n is 1; or $R^3$ is methyl; or $R^4$ is hydrogen, $C_{1-6}$alkyl; phenylmethyl; pyridinylmethyl; 5-methyl-2-furanylmethyl or 2-ethoxyethyl; or $R^5$ is hydrogen, methylaminocarbonyl or phenylaminocarbonyl; or $R^6$ is $C_{1-6}$alkyl; or $R^5$ and $R^6$ taken together may form a bivalent radical of formula (b-3) or (b-6) wherein one hydrogen atom of said bivalent radicals may be replaced by methyl.

11. A composition according to claim 10 wherein
$R^4$ is hydrogen, $C_{1-4}$alkyl, phenylmethyl, 2-pyridinylmethyl or 2-ethoxyethyl; or $R^5$ is hydrogen; or $R^6$ is methyl; or $R^5$ and $R^6$ taken together may form a bivalent radical of formula (b-3) wherein one hydrogen atom of said bivalent radical may be replaced by methyl.

12. A composition according to claim 7 wherein the compound is selected from 2-amino-5-[2-[4-[[1-[[5-(hydroxymethyl)-2-furanyl]methyl]-1H-benzimidazol-2-yl]amino]-1-piperidinyl]ethyl]-3,6-dimethyl-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-(methylamino)-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-[(2-pyridinylmethyl)amino]-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-(propylamino)-4(3H)-pyrimidinone, the pharmaceutically acceptable acid addition salts and the possible stereochemically isomeric forms thereof.

13. A method of treating warm-blooded animals suffering from allergic diseases, which method comprises the administration to said warm-blooded animals of an antiallergically effective amount of a compound as claimed in claim 1.

14. A method according to claim 13 wherein
$R^1$ is hydrogen, ($Ar^1$)$C_{1-6}$alkyl or $C_{1-6}$alkyloxy$C_{1-6}$alkyl; or B is NH, $CH_2$, O or S; or $R^2$ is hydrogen; or $R^3$ is $C_{1-6}$alkyl; or $R^5$ is hydrogen, $C_{1-6}$alkylaminocarbonyl or phenylaminocarbonyl; or $R^6$ is $C_{1-6}$alkyl; or $R^5$ and $R^6$ taken together may form a bivalent radical of formula (b-1) to (b-6) wherein one hydrogen atom of said radicals (b-1) to (b-6) may be replaced by $C_{1-6}$alkyl; or $Ar^1$ is phenyl optionally substituted with halo; furanyl optionally substituted with $C_{1-6}$alkyl and/or hydroxy$C_{1-6}$alkyl; pyridinyl; or thiazolyl.

15. A method according to claim 14 wherein
—$A^1$=$A^2$—$A^3$=$A^4$— is a bivalent radical having the formula (a-1) wherein one or two hydrogen atoms each independently from one another may be replaced by halo, $C_{1-4}$alkyl or $C_{1-4}$alkyloxy; (a-2); (a-6) wherein one hydrogen atom may be replaced by $C_{1-4}$alkyl; or (a-7) wherein one hydrogen atom may be replaced by hydroxy; or $R^1$ is hydrogen, ($Ar^1$)$C_{1-4}$alkyl or $C_{1-4}$alkyloxy$C_{2-4}$alkyl; and/or Alk is 1,2-ethanediyl; or $R^3$ is $C_{1-4}$alkyl; or $R^4$ is hydrogen, $C_{1-6}$alkyl, phenyl$C_{1-4}$alkyl, pyridinyl$C_{1-4}$alkyl, 5-methyl-2-furanyl$C_{1-4}$alkyl or $C_{1-4}$alkyloxy$C_{2-4}$alkyl; or $R^5$ is hydrogen, $C_{1-4}$alkylaminocarbonyl or phenylaminocarbonyl; or $R^6$ is $C_{1-6}$alkyl; or $R^5$ and $R^6$ taken together may form a bivalent radical of formula (b-1); (b-3); (b-5) or (b-6), wherein one hydrogen atom of said radicals (b-3), (b-5) and (b-6) may be replaced by $C_{1-4}$alkyl; or $Ar^1$ is phenyl optionally substituted with halo; furanyl substituted with $C_{1-4}$alkyl and/or hydroxy$C_{1-4}$alkyl; pyridinyl; or thiazolyl.

16. A method according to claim 15 wherein
—$A^1$=$A^2$—$A^3$=$A^4$— is a bivalent radical having the formula (a-1) or (a-2); or $R^1$ is 4-fluorophenylmethyl; 5-methyl-2-furanylmethyl; 5-hydroxymethyl-2-furanylmethyl or 2-ethoxyethyl;

B is NH or $CH_2$; or n is 1; or $R^3$ is methyl; or $R^4$ is hydrogen, $C_{1-6}$alkyl; phenylmethyl; pyridinylmethyl; 5-methyl-2-furanylmethyl or 2-ethoxyethyl; or $R^5$ is hydrogen, methylaminocarbonyl or phenylaminocarbonyl; or $R^6$ is $C_{1-6}$alkyl; or $R^5$ and $R^6$ taken together may form a bivalent radical of formula (b-3) or (b-6) wherein one hydrogen atom of said bivalent radicals may be replaced by methyl.

17. A method according to claim 16 wherein
$R^4$ is hydrogen, $C_{1-4}$alkyl, phenylmethyl, 2-pyridinylmethyl or 2-ethoxyethyl; or $R^5$ is hydrogen; or $R^6$ is methyl; or $R^5$ and $R^6$ taken together may form a bivalent radical of formula (b-3) wherein one hydrogen atom of said bivalent radical may be replaced by methyl.

18. A method according to claim 13 wherein the compound is selected from 2-amino-5-[2-[4-[[1-[[5-(hydroxymethyl)-2-furanyl]methyl]-1H-benzimidazol-2-yl]amino]-1-piperidinyl]ethyl]-3,6-dimethyl-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-(methylamino)-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-[(2-pyridinylmethyl)amino]-4(3H)-pyrimidinone, 5-[2-[4-[[1-[[5-(hydroxymethyl)-2-furanyl]methyl]-1H-benzimidazol-2-yl]amino]-1-piperidinyl]ethyl]-3,6-dimethyl-2-(propylamino)-4(3H)-pyrimidinone, the pharmaceutically acceptable acid addition salts and the possible stereochemically isomeric forms thereof.

* * * * *